United States Patent [19]
Warner et al.

[11] Patent Number: 5,716,327
[45] Date of Patent: Feb. 10, 1998

[54] BODY WALL RETRACTION SYSTEM FOR WIDE CAVITY RETRACTION

[75] Inventors: Robert D. Warner, Cupertino; Albert K. Chin, Palo Alto; Tim J. Kovac, Los Gatos, all of Calif.

[73] Assignee: Origin Medsystems, Inc., Menlo Park, Calif.

[21] Appl. No.: 671,828

[22] Filed: Jun. 25, 1996

Related U.S. Application Data

[63] Continuation of Ser. No. 408,102, Mar. 21, 1995, abandoned, which is a continuation of Ser. No. 128,477, Sep. 28, 1993, abandoned, which is a continuation-in-part of Ser. No. 890,033, May 28, 1992, abandoned, and a continuation-in-part of Ser. No. 62,707, May 18, 1993, Pat. No. 5,520,609, which is a continuation of Ser. No. 706,781, May 29, 1991, abandoned.

[51] Int. Cl.$^6$ ............................................. A61B 17/02
[52] U.S. Cl. ................................. 600/204; 600/215
[58] Field of Search .......................... 606/198, 191, 606/151, 157, 158, 205, 207; 600/204, 215, 229

[56] References Cited

U.S. PATENT DOCUMENTS

| | | | |
|---|---|---|---|
| 1,060,350 | 4/1913 | Miller . | |
| 1,275,520 | 8/1918 | Bell . | |
| 1,618,261 | 2/1927 | Arbogast . | |
| 1,798,124 | 3/1931 | Hunn | 600/204 |
| 1,947,649 | 2/1934 | Kadavy | 128/20 |
| 2,663,020 | 12/1953 | Cushman | 128/303 |
| 2,841,148 | 7/1958 | Kadavy | 128/303 |
| 3,039,468 | 6/1962 | Price | 128/347 |
| 3,460,539 | 8/1969 | Anhald, Sr. | 128/303.17 |
| 3,626,949 | 12/1971 | Shute | 128/344 |
| 3,631,859 | 1/1972 | Crutchfield | 606/158 |
| 3,717,151 | 2/1973 | Collett | 128/347 |
| 3,774,596 | 11/1973 | Cook | 128/5 |
| 3,782,370 | 1/1974 | McDonald | 128/20 |
| 3,831,587 | 8/1974 | Boyd | 128/6 |
| 3,863,639 | 2/1975 | Kleaveland | 128/303 R |
| 3,868,957 | 3/1975 | Doddington | 606/158 |
| 3,961,632 | 6/1976 | Moossun | 128/347 |
| 4,052,980 | 10/1977 | Grams et al. | 128/18 |
| 4,077,412 | 3/1978 | Moossun | 128/347 |

(List continued on next page.)

FOREIGN PATENT DOCUMENTS

| | | | |
|---|---|---|---|
| B-516114 | 5/1981 | Australia | A61B 10/00 |
| A 0 010 650 | 5/1980 | European Pat. Off. | A61M 31/00 |
| A 0 246 086 | 11/1987 | European Pat. Off. | A61B 17/02 |
| A 0 251 976 | 1/1988 | European Pat. Off. | A61M 29/02 |
| A 0 275 230 | 7/1988 | European Pat. Off. | A61M 25/00 |
| 0 464 463 A1 | 1/1992 | European Pat. Off. | A61B 17/28 |

(List continued on next page.)

OTHER PUBLICATIONS

G. Keen MS, FRCS, (ed.) "Operative Surgery & Management," pp. 334–335, (2nd. ed., Wright, Bristol, 1987).

R.F. Rintoul (ed.), "Farquharson's Textbook of Operative Surgery" pp. 286–289, (7th ed., Churchill Livingstone, New York, 1986).

(List continued on next page.)

Primary Examiner—Michael H. Thaler
Attorney, Agent, or Firm—Limbach & Limbach

[57] ABSTRACT

A method and apparatus for creating a surgical work space by lifting the abdominal wall and retracting abdominal organs during surgery utilizes a lifting body having two or more retraction rods supported by the lifting body. The rods are designed to be introduced into the abdominal cavity through a laparoscopic puncture opening and to be extended within the abdominal cavity to provide a lifting area. In the preferred embodiment, a pair of retraction rods disposed with the bores and substantially parallel to each other are inserted into the abdominal cavity through an incision in the abdominal wall. The retraction rods are spread apart from each other while their parallel orientation is maintained. The lifting body is connected to a lifting arm and lifted, causing the retraction rods to lift and support the abdominal wall.

19 Claims, 13 Drawing Sheets

U.S. PATENT DOCUMENTS

| | | | |
|---|---|---|---|
| 4,083,369 | 4/1978 | Sinnreich | 128/276 |
| 4,183,102 | 1/1980 | Guiset | 604/101 X |
| 4,240,433 | 12/1980 | Bordow | 128/347 |
| 4,254,762 | 3/1981 | Yoon | 128/4 |
| 4,291,687 | 9/1981 | Sinnreich | 128/129 |
| 4,357,940 | 11/1982 | Muller | 128/303 R |
| 4,430,076 | 2/1984 | Harris | 605/96 |
| 4,447,227 | 5/1984 | Kotsanis | 604/95 |
| 4,459,978 | 7/1984 | Kotsanis | 128/20 |
| 4,502,485 | 3/1985 | Burgin | 128/20 X |
| 4,535,773 | 8/1985 | Yoon | 604/51 |
| 4,572,179 | 2/1986 | Teitelbaum et al. | 606/207 |
| 4,598,699 | 7/1986 | Garren et al. | 128/4 |
| 4,601,710 | 7/1986 | Moll | 604/165 |
| 4,654,030 | 3/1987 | Moll et al. | 604/165 |
| 4,662,955 | 5/1987 | Fakrai | 128/20 |
| 4,693,243 | 9/1987 | Buras | 128/207.25 |
| 4,705,040 | 11/1987 | Mueller et al. | 128/334 R |
| 4,709,697 | 12/1987 | Muller | 128/303 R |
| 4,744,363 | 5/1988 | Hasson | 128/331 |
| 4,763,635 | 8/1988 | Rockey | 604/101 X |
| 4,765,331 | 8/1988 | Petruzzi et al. | 128/303.14 |
| 4,775,371 | 10/1988 | Mueller, Jr. | 604/280 |
| 4,779,611 | 10/1988 | Grooters et al. | 128/4 |
| 4,919,152 | 4/1990 | Ger | 128/898 |
| 4,944,443 | 7/1990 | Oddsen et al. | 227/19 |
| 4,966,583 | 10/1990 | Debbas | 604/98 |
| 4,984,564 | 1/1991 | Yuen | 128/20 |
| 5,002,557 | 3/1991 | Hasson | 606/191 |
| 5,007,898 | 4/1991 | Rosenbluth et al. | 604/54 |
| 5,014,407 | 5/1991 | Boughten et al. | 606/207 X |
| 5,062,847 | 11/1991 | Barnes | 606/194 |
| 5,082,005 | 1/1992 | Kaldany | 128/850 |
| 5,083,576 | 1/1992 | Ruiz-Razura et al. | 128/898 |
| 5,100,426 | 3/1992 | Nixon | 606/170 |
| 5,122,122 | 6/1992 | Allgood | 604/174 X |
| 5,122,155 | 6/1992 | Ederbach | 606/213 |
| 5,133,724 | 7/1992 | Wilson et al. | 606/151 |
| 5,141,515 | 8/1992 | Ederbach | 128/887 |
| 5,152,279 | 10/1992 | Wilk | 600/204 |
| 5,163,949 | 11/1992 | Bonutti | 606/192 |
| 5,176,128 | 1/1993 | Andrese | 128/20 |
| 5,176,692 | 1/1993 | Wilk et al. | 606/151 |
| 5,176,697 | 1/1993 | Hasson et al. | 606/191 |
| 5,183,033 | 2/1993 | Wilk | 128/20 |
| 5,183,463 | 2/1993 | Debbas | 604/98 |
| 5,183,464 | 2/1993 | Debrul et al. | 128/3 |
| 5,188,630 | 2/1993 | Christaudias | 606/191 |
| 5,195,505 | 3/1993 | Josefsen | 128/20 |
| 5,195,506 | 3/1993 | Hulfish | 600/204 |
| 5,195,507 | 3/1993 | Bilweis | 604/97 |
| 5,197,948 | 3/1993 | Ghodsian | 604/30 |
| 5,209,747 | 5/1993 | Knoepfler | 606/205 X |
| 5,250,074 | 10/1993 | Wilk et al. | 606/158 X |
| 5,254,130 | 10/1993 | Poncet et al. | 606/205 X |
| 5,269,753 | 12/1993 | Wilk | 604/49 |
| 5,271,385 | 12/1993 | Bailey | 128/20 |
| 5,275,608 | 1/1994 | Forman et al. | 606/205 X |
| 5,280,782 | 1/1994 | Wilk | 128/20 |
| 5,284,130 | 2/1994 | Ratliff | 600/229 |
| 5,289,817 | 3/1994 | Williams et al. | 128/20 |
| 5,330,502 | 7/1994 | Hasseler et al. | 606/205 |

FOREIGN PATENT DOCUMENTS

| | | | |
|---|---|---|---|
| 0 449 663 A3 | 3/1992 | European Pat. Off. | A61B 17/02 |
| 0 531 710 A2 | 3/1993 | European Pat. Off. | A61B 1/00 |
| A 2 474 304 | 7/1981 | France | A61B 17/00 |
| A 2 646 088 | 10/1990 | France | A61M 29/04 |
| A 2 688 695 | 5/1992 | France | A61B 17/00 |
| OS 1 516 411 | 7/1969 | Germany . | |
| A 2 847 633 | 5/1979 | Germany | A61B 17/22 |
| U 85 16 286 | 9/1985 | Germany | A61B 17/02 |
| 3600789 | 7/1987 | Germany | 606/151 |
| 91 02 759 U | 7/1991 | Germany | A61B 17/02 |
| U 91-04 383 | 7/1991 | Germany | A61B 17/02 |
| 92 02 305 U | 6/1992 | Germany | A61B 19/00 |
| A 736949 | 5/1980 | U.S.S.R. | A61B 1/00 |
| A 797668 | 1/1981 | U.S.S.R. | A61B 17/02 |
| A 1367947 | 1/1988 | U.S.S.R. | A61B 17/02 |
| A 1577769 | 7/1990 | U.S.S.R. | A61B 17/02 |
| 797 668 | 1/1991 | U.S.S.R. | 128/20 |
| 1690704A1 | 11/1991 | U.S.S.R. | A61B 17/02 |
| A 2 071 502 | 9/1981 | United Kingdom | A61B 17/02 |
| WO-A 91 02 493 | 3/1991 | WIPO | A61B 17/22 |
| WO-A 91/14 392 | 10/1991 | WIPO | A61B 1/32 |

OTHER PUBLICATIONS

Ed. G. Berci, Endoscopy, Appleton–Century–Crofts, 1976, pp. 382–385 and 412.

Unknown—Laparoscopy for Sterilization, Section 1, A Chronology of Laparoscopy.

"New Surgical Procedures for Indirect Hernias"—Product Leaflet for Herniastat ™ disposable automatic surgical stapling device published by Innovative Surgical Devices, Inc., date unknown.

"A Tiny TV Camera is Fast Transforming Gallbladder Surgery," Wall Street Journal, Dec. 10, 1990, p. A1, continued on p. A5.

A Comprehensive Guide to Purchasing [Hospital Supplies], V. Mueller & Co, Chicago, 1956, p. 829.

H. Nagai et al., "A New Method of Laparoscopic Cholecystectomy: An Abdominal Wall Lifting Technique without Pneumoperitoneum," Surgical Laparoscopy and Endoscopy, vol. 1, No. 2, 1991, p. 126.

M.M. Gazayerli, "The Gazayerli Endoscopic Retractor Model 1," Surgical Laparoscopy and Endoscopy, vol. 1, No. 2, 1991, pp. 98–100.

Geza J. Jako & Stephen Rozsos, "Preliminary Report: Endoscopic Laser Microsurgical Removal of Human Gallbladder," J. Laparoendoscopic Surgery, vol. 1, No. 4, 1991.

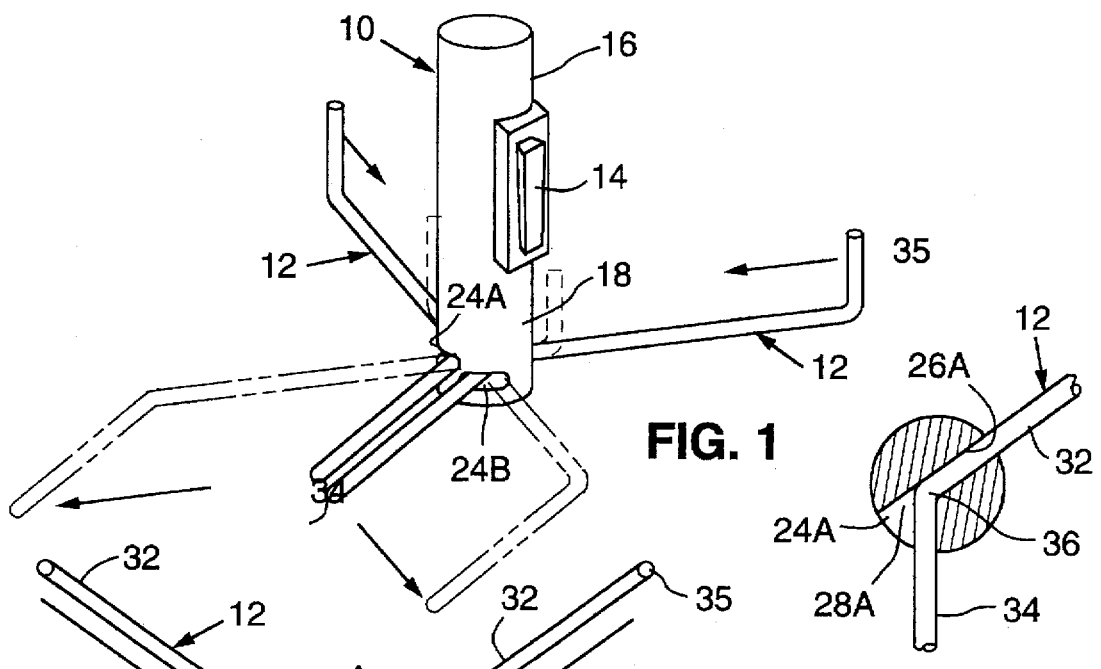
FIG. 1
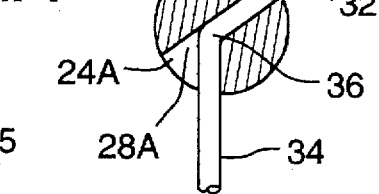
FIG. 5
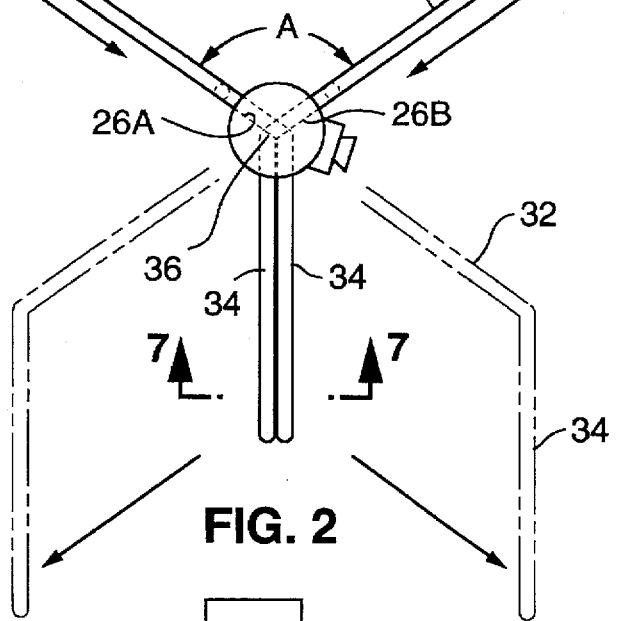
FIG. 2
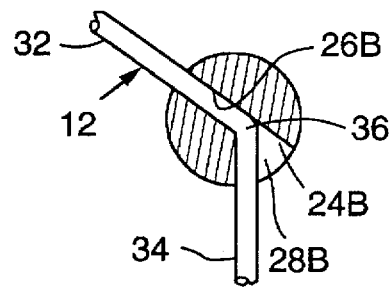
FIG. 6
FIG. 7
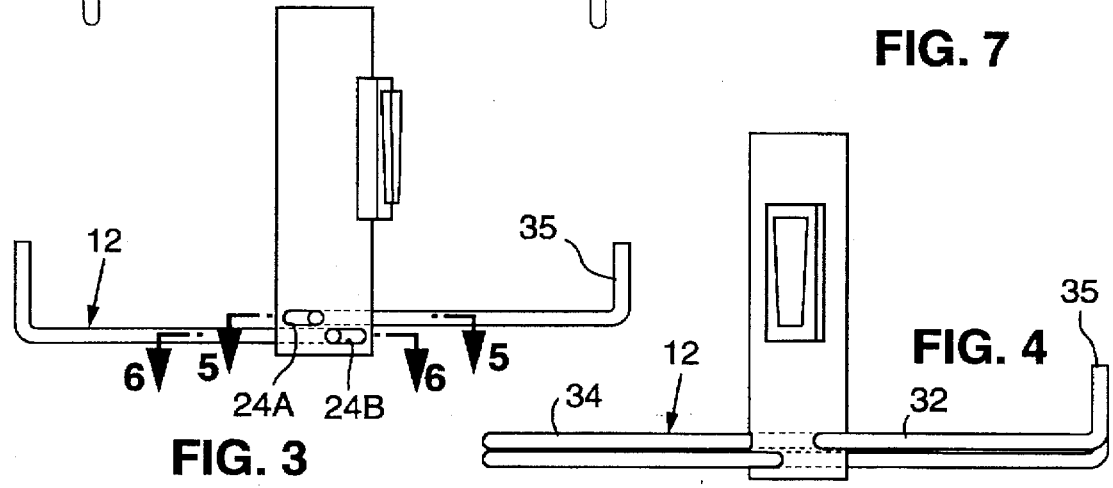
FIG. 3
FIG. 4

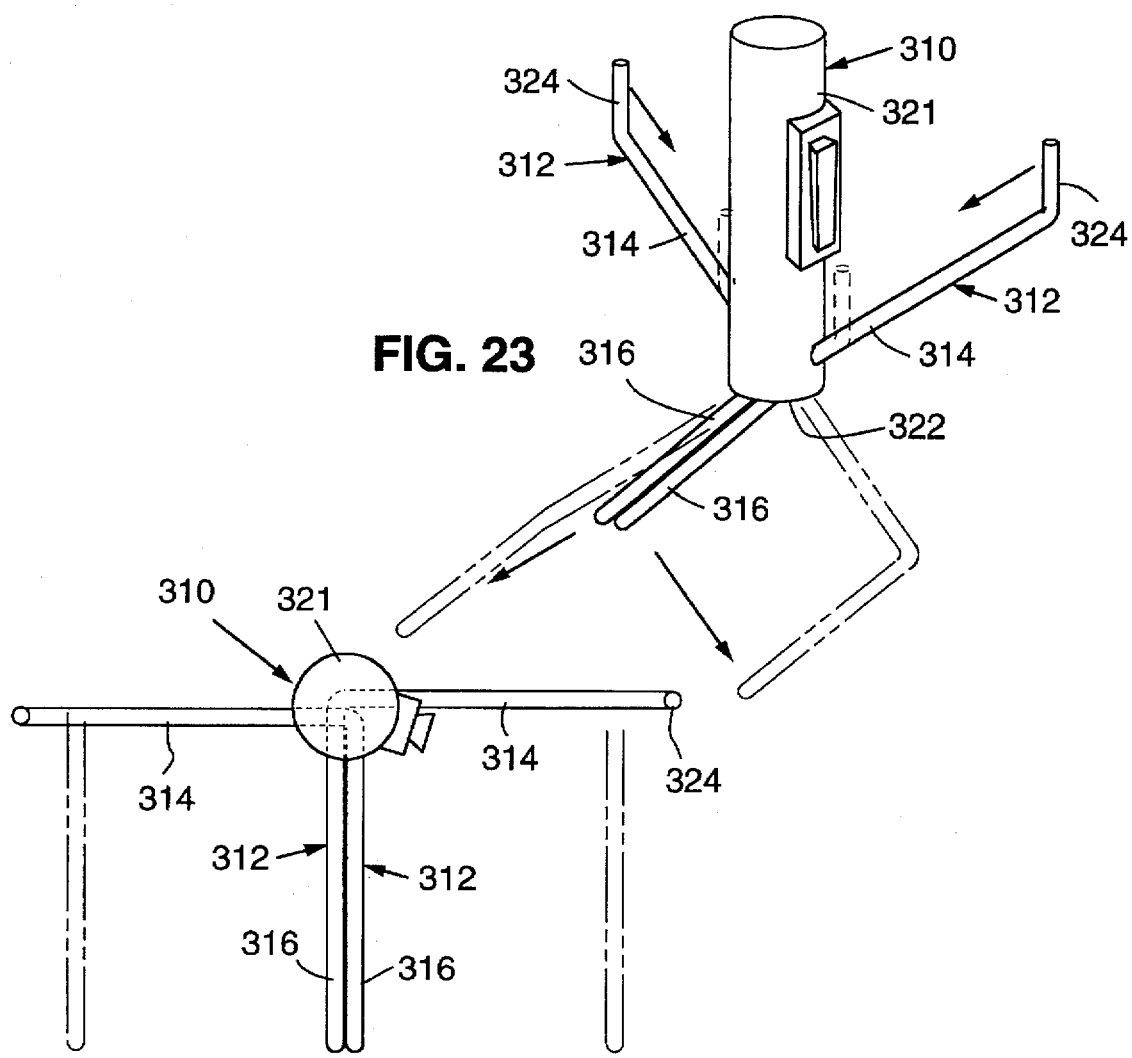
FIG. 23
FIG. 24
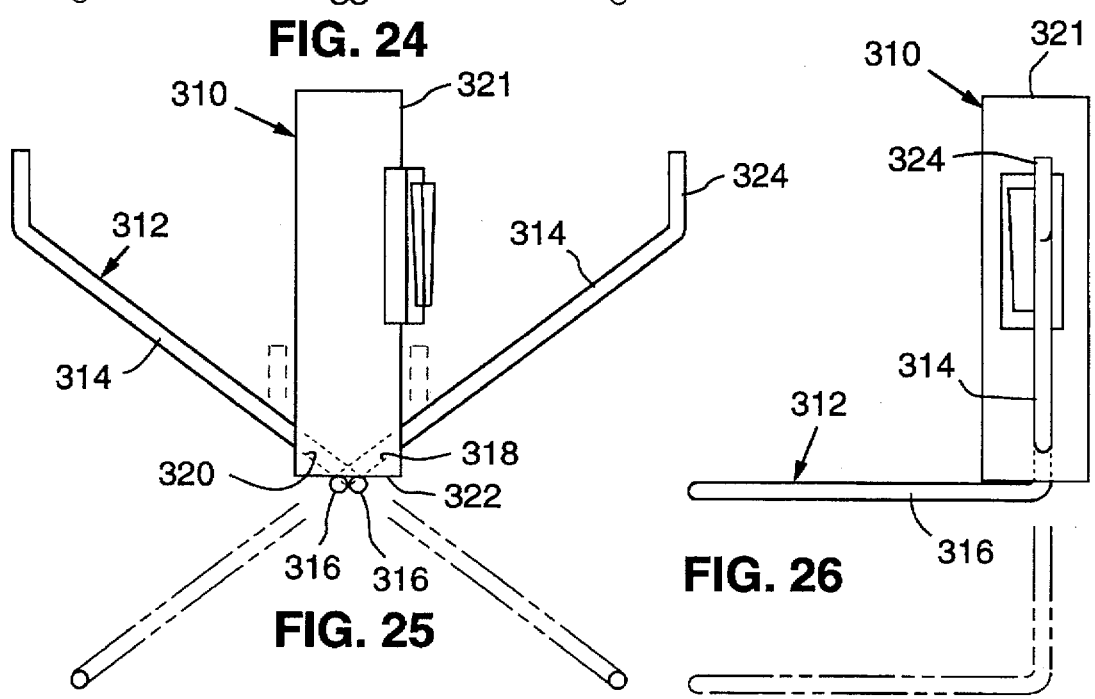
FIG. 25
FIG. 26

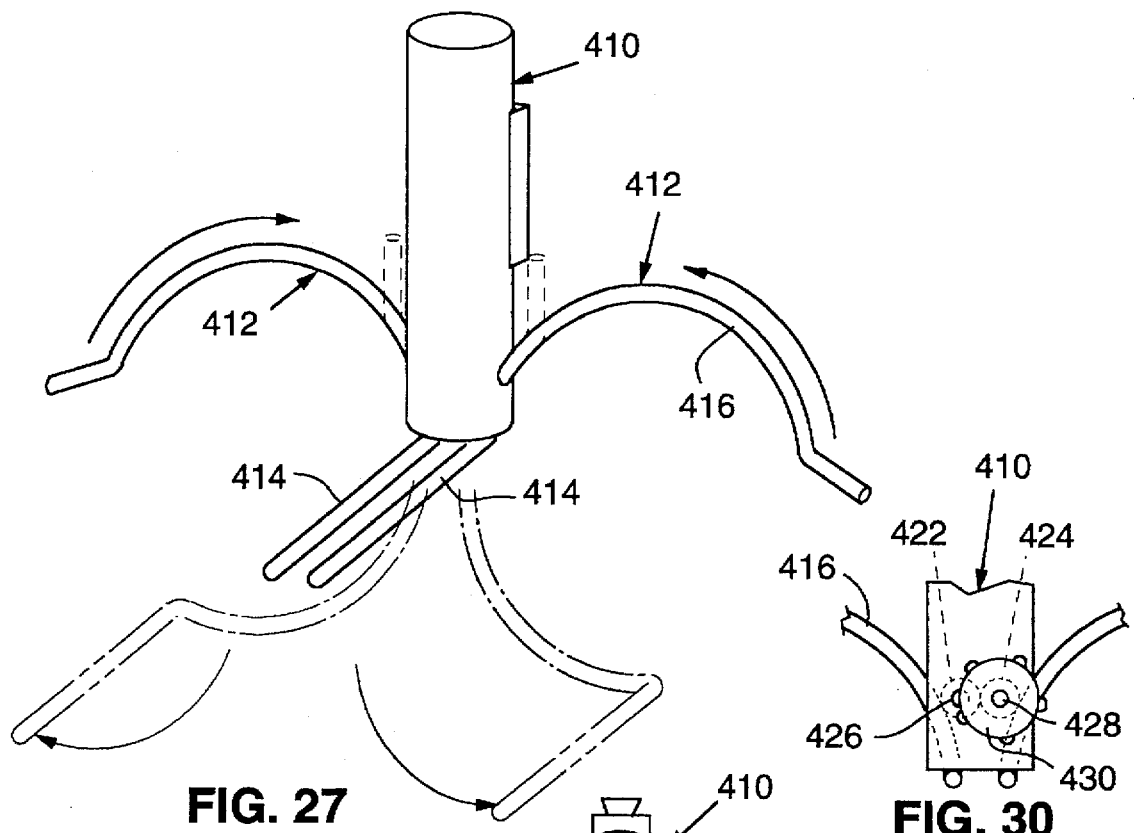
FIG. 27
FIG. 30
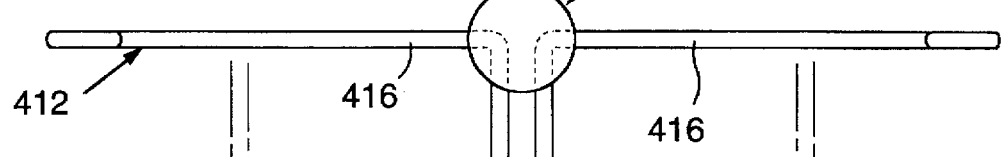
FIG. 28
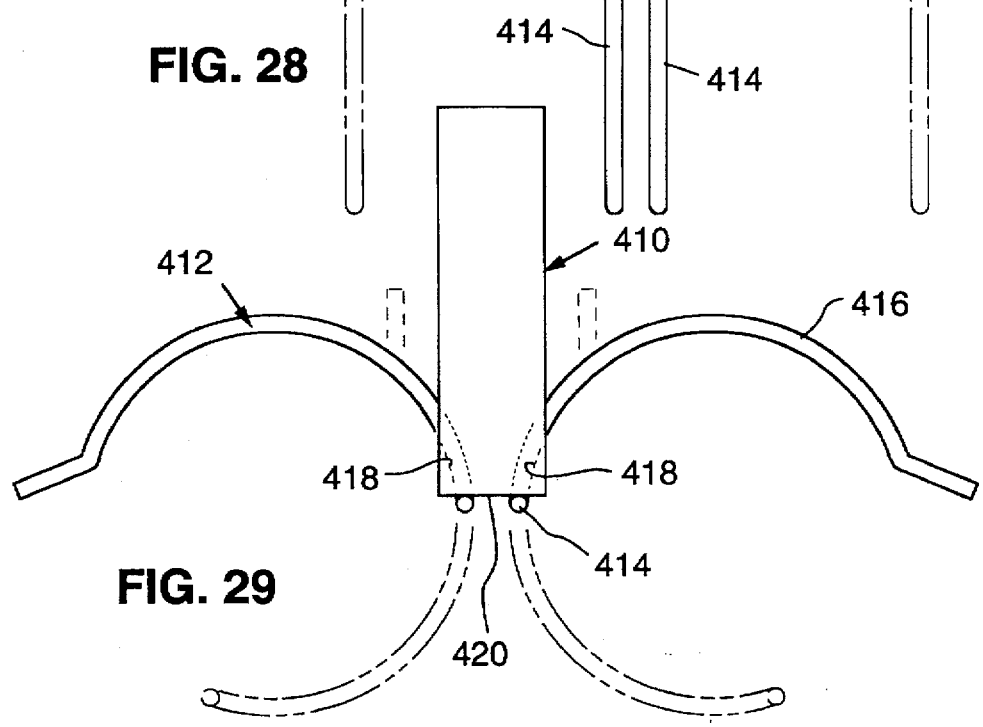
FIG. 29

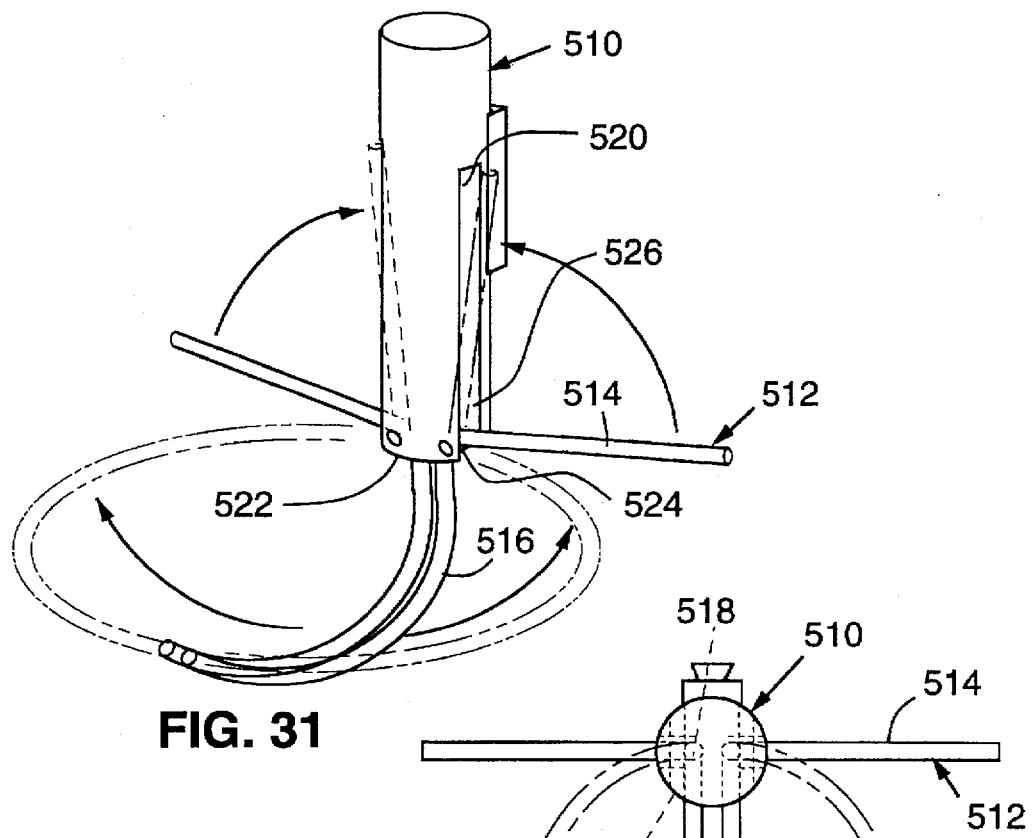
FIG. 31
FIG. 32
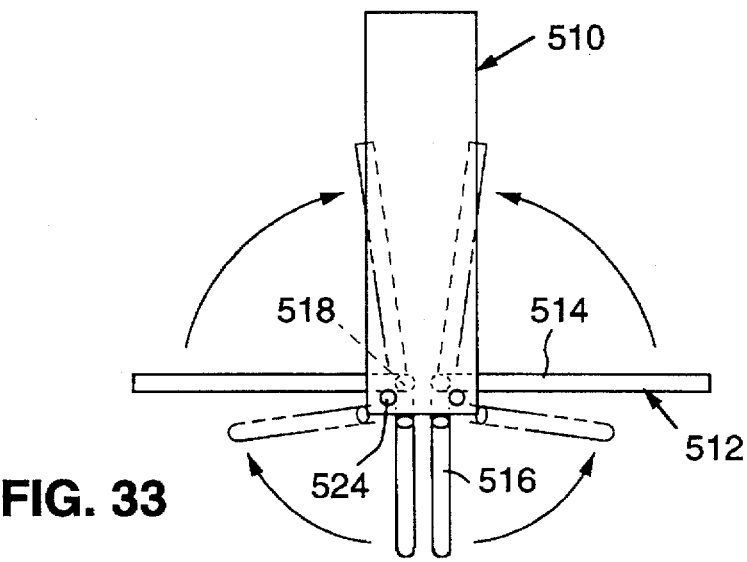
FIG. 33

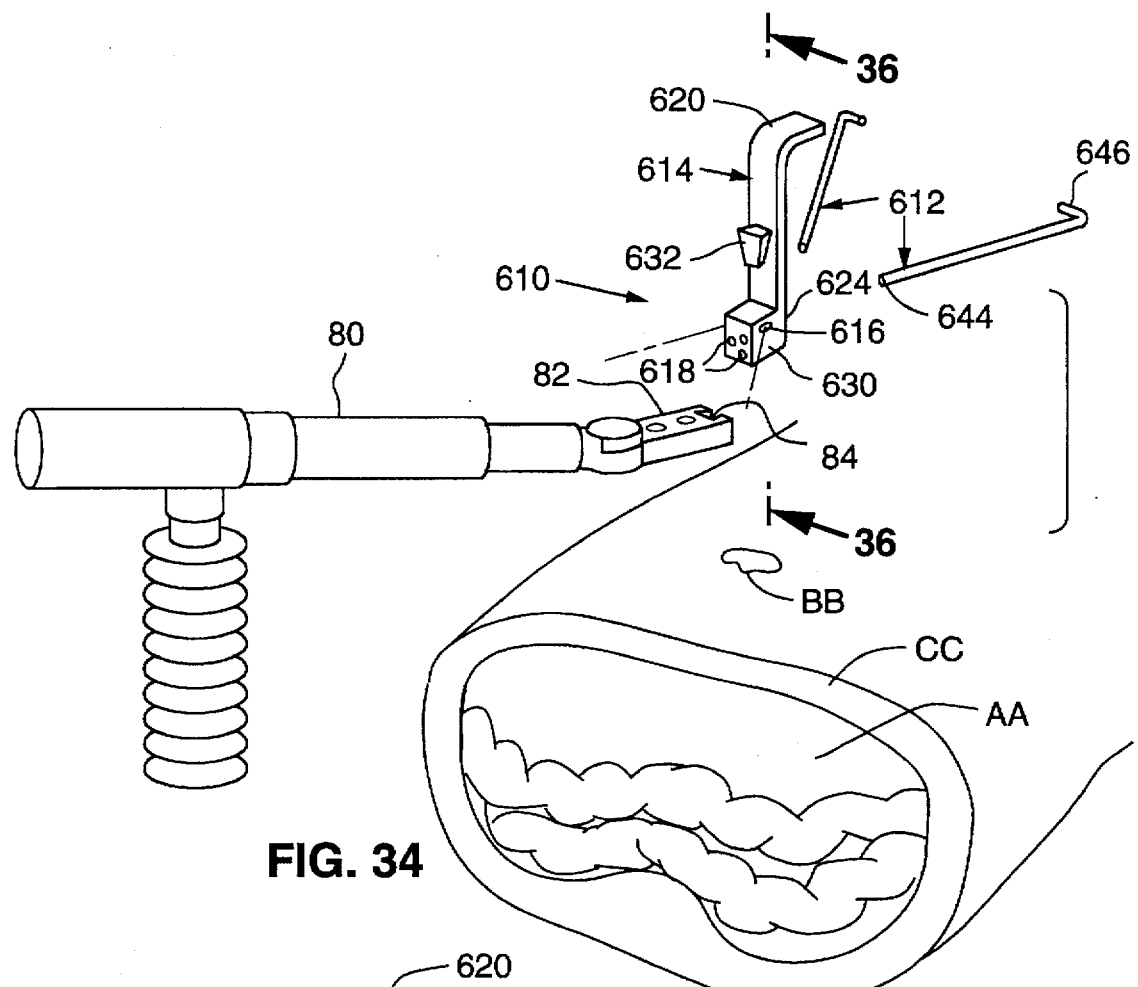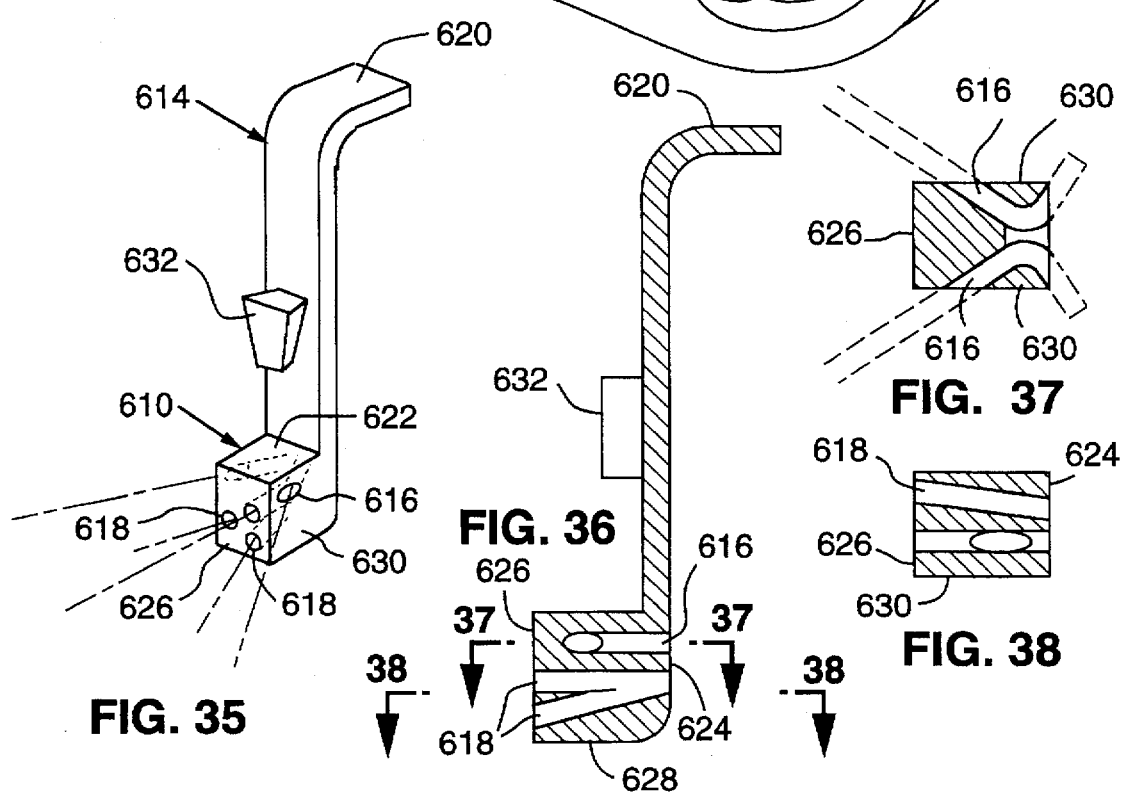
FIG. 34
FIG. 35
FIG. 36
FIG. 37
FIG. 38

BODY WALL RETRACTION SYSTEM FOR WIDE CAVITY RETRACTION

This is a continuation of application Ser. No. 08/408,102 filed Mar. 21, 1995, now abandoned, which was a continuation of Ser. No. 08/128,477 filed Sep. 28, 1993, now abandoned, which was a continuation-in-part of Ser. No. 07/890,033, filed May 28, 1992, now abandoned, and which was also a continuation-in-part of Ser. No. 08/062,707 filed May 18, 1993, now U.S. Pat. No. 5,520,609, which was a continuation of Ser. No. 07/706,781, filed May 29, 1991, now abandoned.

FIELD OF THE INVENTION

The present invention relates to the field of surgical retractors and particularly to lifting the abdominal wall and retracting the abdominal contents during laparoscopic surgery.

BACKGROUND OF THE INVENTION

Laparoscopy dates back to the turn of the 20th Century. Early laparoscopic techniques were used primarily for diagnostic purposes to view the internal organs, without the necessity of conventional surgery. Since the 1930s, laparoscopy has been used for sterilization and, more recently, for suturing hernias. U.S. Pat. Nos. 4,919,152 and 4,944,443 are concerned with techniques for suturing hernias. Another recent innovation is the use of laparoscopic surgery for removing the gallbladder.

In the course of performing laparoscopic procedures in the abdomen, it is necessary to raise the abdominal wall to create space in which to work. A well-known method of raising the abdominal wall is to insufflate the abdominal cavity with a suitable insufflation gas, such as air, or carbon dioxide. A significant disadvantage of gas insufflation is that instruments must be passed into the abdominal cavity through gas-tight seals, which significantly reduce the surgeon's feel of the instruments.

Several mechanical alternatives to gas insufflation have been proposed. The Gazayerli Endoscopic Retractor Model 1, described in SURGICALLAPAROSCOPY AND ENDOSCOPY, Vol. 1, No. 2, 1991, pages 98-100, has a rigid rod with a hinged blade at the distal end. The blade can rotate through 360 degrees about an axis perpendicular to the long axis of the rod. The blade is aligned with the long axis of the rod for insertion into the abdomen through a small puncture. Once inside the abdomen, the blade is swivelled through about 90 degrees to form a T-shaped structure. The proximal end of the rod can be raised by hand or by a rope, pulley and weight arrangement. Raising the rod causes the blade to engage the abdominal wall and to lift it.

French patent application no. 90-03980 shows a wire structure that is threaded into the abdomen through a small puncture to engage and to lift the abdominal wall. The application also shows a fan retractor that has a first angle-shaped member having a first leg that engages with the abdominal wall, a tubular second leg having a bore, and a third leg, remote from the first leg, that has a hook-shaped member on its end distal from the second leg. A second angle-shaped member has a first leg that engages with the abdominal wall, a second leg that pivots within the bore of the second leg of the first angle-shaped member, and a third leg, remote from the first leg, that serves as an operating lever for the second angle-shaped member. The first legs of the angle-shaped members are closed together to insert them into the abdominal cavity through an incision. The third leg of the second angle-shaped member is then operated to spread the first leg of the second angle-shaped member apart from the first leg of the first angle-shaped member. The first legs are engaged with the peritoneum inside the abdominal cavity. A lifting force is then applied to the hook-shaped member to lift the retractor and hence to lift the abdominal wall.

U.S. patent application Ser. No. 07/706,781, the application of which this application is a Continuation-in-Part, describes a number of different mechanical devices that are inserted through one or more punctures into the abdomen. All or part of the device is then lifted to lift the abdominal wall away from the underlying abdominal organs. One of the devices described in this application is a fan retractor that is inserted in a closed condition into the abdomen, spread apart once inside the abdomen, and brought into contact with the peritoneum inside the abdomen. The fan retractor is then raised by a lifting arm to lift the abdominal wall. Another of the devices is an inflatable device which is introduced laparoscopically and, once in place, inflated to engage and lift an extensive area of the abdominal wall.

One disadvantage of presently known retraction systems is that the triangular lifting area provided by fan retractors is sometimes not sufficiently broad to allow visualization of a wide region of the abdominal cavity. Also, because these fan retractors utilize a pair of retraction rods which must be pivoted simultaneously to a predetermined separation, they do not allow the surgeon to choose a retraction rod configuration which is most suitable for the abdominal region being treated. Finally, during deployment of fan retractors the pivoting retractors can sometimes catch on tissue located in their path thus necessitating removal and re-placement of the retractor.

OBJECT AND SUMMARY OF THE INVENTION

It is an object of the present invention to provide an apparatus and method for mechanically retracting the abdominal wall to provide visualization of a wide cavity within the abdominal region and working space within it. It is also an object of the invention to provide an apparatus and method for retracting abdominal contents away from the working space. Another object of the present invention is to provide an abdominal retraction device which offers a selection of retractor positions. Yet another object is to provide a mechanical retractor with lifting arms which may be placed in spaced relationship without pivotal movement relative to one another.

An abdominal wall retractor according to the present invention has a lifting body and retraction rods that are capable of extending individually from the lifting body into the abdominal cavity. The retraction rods are advanced into the abdominal cavity where they are used to raise and support the abdominal wall, thus creating a work space for laparoscopic surgery.

BRIEF DESCRIPTION OF THE DRAWINGS

FIG. 1 is a perspective view of a first exemplary embodiment of the retraction system according to the invention showing the retraction rods in the closed position and further showing, in phantom lines, the retraction rods in the open position.

FIG. 2 is a top view of the first embodiment of FIG. 1 showing the retraction rods in the closed position and further showing, in phantom lines, the retraction rods in the open position.

FIG. 3 is a front view of the first embodiment of FIG. 1.

FIG. 4 is a side view of the first embodiment of FIG. 1.

FIGS. 5 and 6 are cross-sectional top views of the first embodiment of FIG. 1 taken along the planes designated 5—5 and 6—6, respectively, in FIG. 3.

FIG. 7 is a cross-sectional view of a retraction rod taken along the plane designated 7—7 in FIG. 2.

FIG. 23 is a perspective view of a fifth embodiment according to the present invention, showing the retraction rods in the closed position and further showing, in phantom lines, the retraction rods in the open position.

FIG. 24 is a top view of the fifth embodiment of FIG. 23 showing the retraction rods in the closed position and further showing, in phantom lines, the retraction rods in the open position.

FIG. 25 is a front view of the fifth embodiment of FIG. 23 showing the retraction rods in the closed position and further showing, in phantom lines, the retraction rods in the open position.

FIG. 26 is a side view of the fifth embodiment of FIG. 23 showing the retraction rods in the closed position and further showing, in phantom lines, the retraction rods in the open position.

FIG. 27 is a perspective view of a sixth embodiment according to the invention, showing the retraction rods in the closed position and further showing, in phantom lines, the retraction rods in the open position.

FIG. 28 is a top view of the sixth embodiment of FIG. 27 showing the retraction rods in the closed position and further showing, in phantom lines, the retraction rods in the open position.

FIG. 29 is a top view of the sixth embodiment of FIG. 27 showing the retraction rods in the closed position and further showing, in phantom lines, the retraction rods in the open position.

FIGS. 30 is a partial front view of a modified version of the sixth embodiment of FIG. 27 showing a roller system for simultaneously extending the retraction rods.

FIG. 31 is a perspective view of a seventh embodiment according to the invention showing the retraction rods in the closed position and further showing, in phantom lines, the retraction rods in the open position.

FIG. 32 is a top view of the seventh embodiment of FIG. 31 showing the retraction rods in the closed position and further showing, in phantom lines, the retraction rods in the open position.

FIG. 33 is a front view of the seventh embodiment of FIG. 31 showing the retraction rods in the closed position and further showing, in phantom lines, the retraction rods in the open position.

FIG. 34 is a perspective view, schematically showing an eighth embodiment of a retraction system according to the invention prior to its insertion into the abdominal cavity.

FIG. 35 is a perspective view of the lifting body and handle of the eighth embodiment of FIG. 34.

FIG. 36 is a cross-sectional side view of the lifting body and handle of the eighth embodiment taken along the plane designated as 36—36 in FIG. 34.

FIG. 37 is a cross-sectional top view of the lifting body of the eighth embodiment taken along the plane designated as 37—37 in FIG. 36.

FIG. 38 is a cross-sectional top view of the lifting body of the eighth embodiment taken along the plane designated as 38—38 in FIG. 36.

DETAILED DESCRIPTION OF THE INVENTION

The present invention provides a lifting body having retraction rods which are selectively extensible therefrom for supporting the abdominal wall during lifting. The invention will be described with reference to nine exemplary embodiments.

FIGS. 1–10 show the first embodiment of the present retraction system. The first embodiment is comprised of a cylindrical lifting body 10 having proximal and distal portions 16 and 18, respectively. The distal portion 18 of the cylindrical lifting body may be connected to the proximal portion 16 by a swivel connector (see FIGS. 15–18) which enables the distal portion to swivel about its axis relative to the proximal portion. The swivel connector preferably has a locking mechanism to prevent swiveling during lifting of the abdominal wall.

Figure 10:
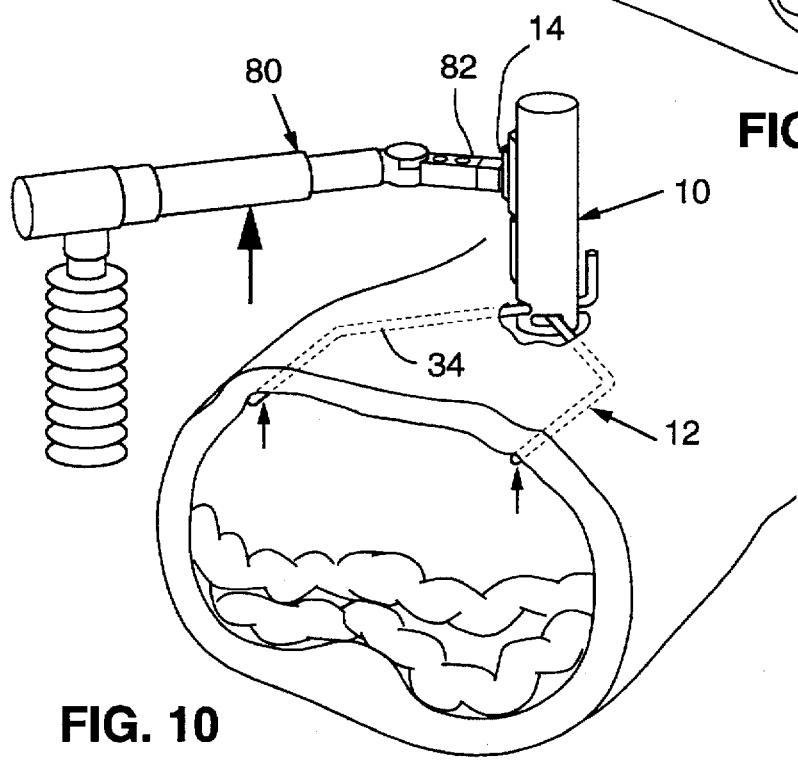
Figure 11:
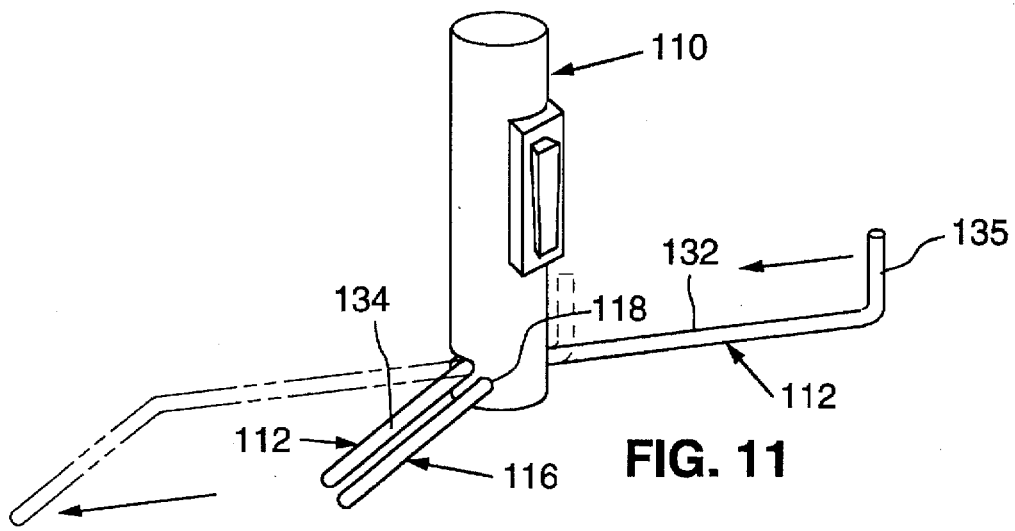
FIG. 11 is a perspective view of a second embodiment of the invention showing the retraction rods in the closed position and further showing, in phantom lines, the retraction rods in the open position.

A dovetail connector 14 is mounted on the proximal portion 16 for connecting the fan retractor to a lifting bar or holding bar 80 (See FIG. 10). The dovetail connector is constructed to form a positive lock with a dovetail slot formed in a lifting bar adaptor 82 (see FIG. 10).

Within the distal portion 18 of the cylindrical lifting body 10 are a pair of cut-out sections, designated 24A and 24B. The cut-out sections 24A, 24B are substantially perpendicular to the longitudinal axis of the lifting body. As shown in FIG. 3, one cutout section 24A is positioned proximal and lateral of the other cut-out section 24B.

As can be appreciated upon reference to FIGS. 5 and 6, each cut-out section is a mirror-image of the other. Describing the cut-out sections with reference to FIG. 5, cut-out section 24A is comprised of a bore 26A which passes through the cylindrical lifting body, converges towards midline m, and connects with a cut-out triangular section 28A which extends to the perimeter of the cylindrical lifting body. The included angle A, shown in FIG. 2, between the bores 26A, 26B of the cut-out sections is approximately 120°.

Each of the retraction rods used with the first embodiment is comprised of a proximal portion 32 and a distal portion 34 joined at an elbow 36. As shown in FIGS. 2, 5 and 6, the rods are positioned in the cut-out sections 24A, 24B such that their proximal portions 32 pass through the bores 26a, 26B, and their distal portions 34 are situated within the triangular sections 28a, 28B and extend substantially parallel to each other, away from the cylindrical lifting body. As shown in FIG. 4, the rods are configured such that they are substantially perpendicular to the longitudinal axis of the cylindrical lifting body when they are not loaded. At the proximal end of each rod is a short vertical portion 35, which serves as a handle for use in sliding the rods within the bores.

The rods may have square, oval, or "D"-shaped (see FIG. 7) cross-sections, at least at their proximal portions 32, and the bores 26A, 26B in the cylindrical lifting body have corresponding cross-sections (not shown) which prevent the rods from rotating in the bores. The rods are designed such that they will deform slightly downwards during lifting to conform to the shape of the raised abdomen and to thereby distribute the weight of the abdominal wall along the length of the rods. Moreover, the distal sections of the rods preferably bend towards each other slightly during lifting so as to distribute the load naturally along the length of the rods.

The first embodiment allows the surgeon to choose the degree to which the rods will be extended for lifting. Advancing the proximal portions 32 through the cylindrical lifting body 10 as indicated by arrows in FIGS. 1 and 2 causes distal portions 34 to advance further out of the cut-out sections 24A, 24B and to move laterally away from each other. The apparatus may be provided with a locking device which enables the rods to be locked in place after they have been extended to the desired position.

Figure 8:
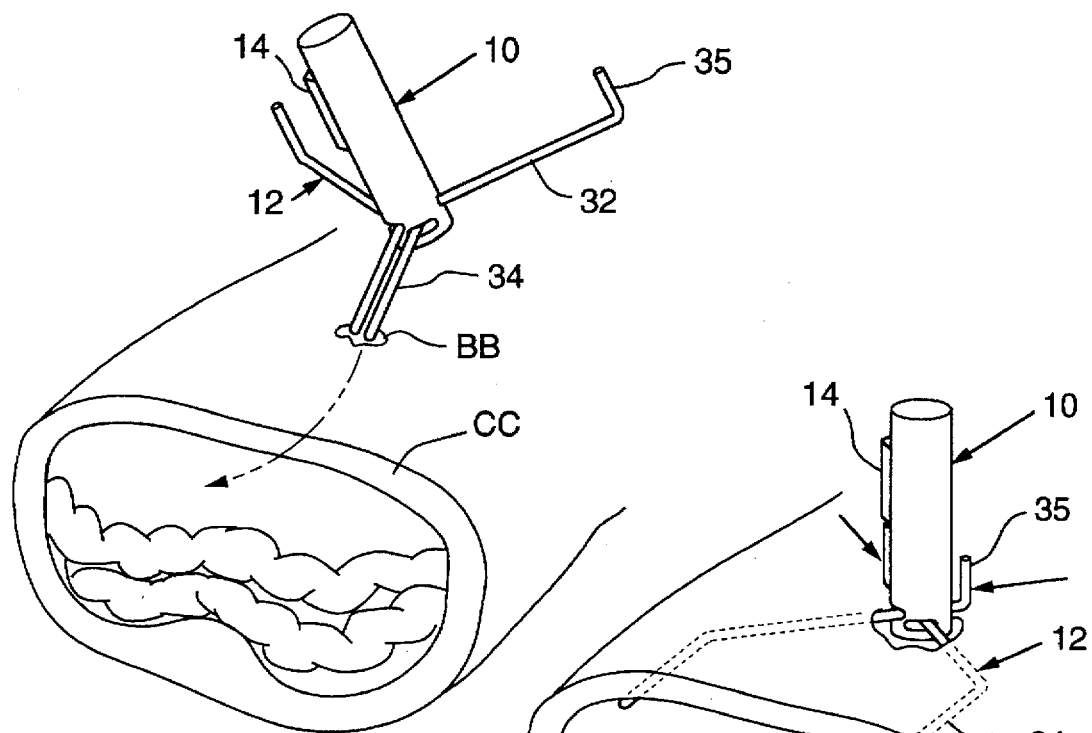
FIGS. 8 through 10 are a series of perspective views schematically showing use of the first embodiment of FIG. 1.
Figure 9:
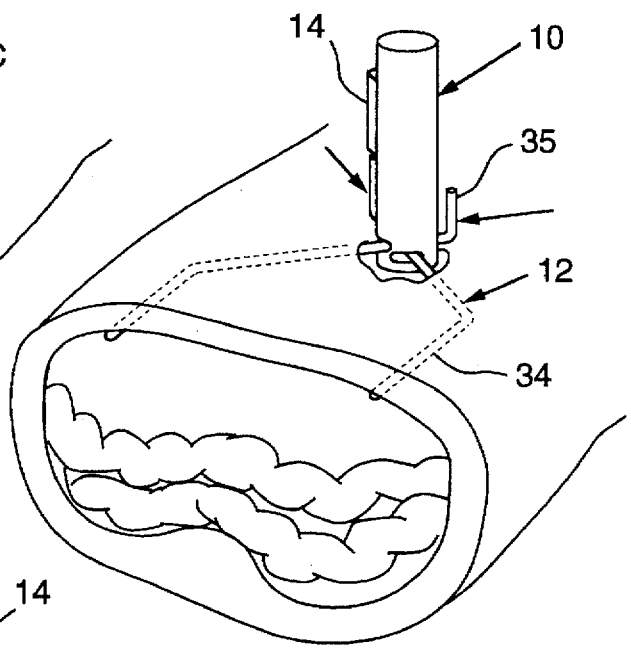

Clinical use of the first embodiment will next be described with reference to FIGS. 8 through 10. The rods are first withdrawn in a proximal direction to position the distal portions 34 immediately adjacent to one another as shown in FIG. 8. When the rods are withdrawn, the proximal portions 32 diverge from the bore entrances at the rear of the cylindrical body as shown in FIG. 8. The distal portions 34 of the rods are inserted into a puncture opening BB in the abdominal wall CC at a slightly downward angle. The cylindrical body 10 is then pivoted upwards to orient the rods such that they are substantially parallel to the horizontal plane. The rods are then advanced through the bores in a distal direction, as indicated by arrows in FIG. 9, causing the distal ends to spread apart while maintaining their parallel relationship. Once the distal portions have been spread to the desired distance, the dovetail connector 14 is connected to a mechanical lifting arm 80, shown in FIG. 10, which is then raised to elevate the abdominal cavity. The D-shaped cross-sections of the bores (not shown) prevent the similarly shaped rods from rotating during loading.

Several alternative rod configurations may be devised according to the present invention. A second embodiment is shown in FIGS. 11–14. This configuration is asymmetrical in design to allow for distension of the left or right abdominal cavity. The cavity-specific configuration is comprised of one fixed, substantially straight, rod 116 and one angular rod 112 which is preferably identical in design to the rods of the first embodiment. The straight rod 116 is secured within a bore 118 which passes through the cylindrical body in a direction parallel to midline m.

The angular rod 112 is comprised of an angled proximal portion 132 and a straight distal portion 134 joined at an elbow. At the proximal end of the proximal portion 132 is a handle 135. The angled rod 112 is positioned with the proximal portion 132 slidably disposed within a cut-out section in the cylindrical body 110, which may be identical to the section shown in FIG. 5. The cut-out section 124 is positioned proximal and lateral of bore 118.

Figure 12:
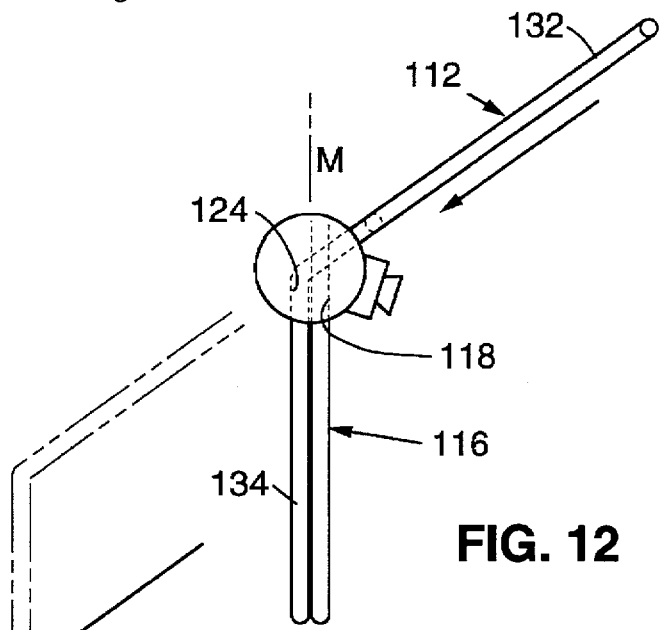
FIG. 12 is a top view of the second embodiment of FIG. 11 showing the retraction rods in the closed position and further showing, in phantom lines, the retraction rods in the open position.
Figure 13:
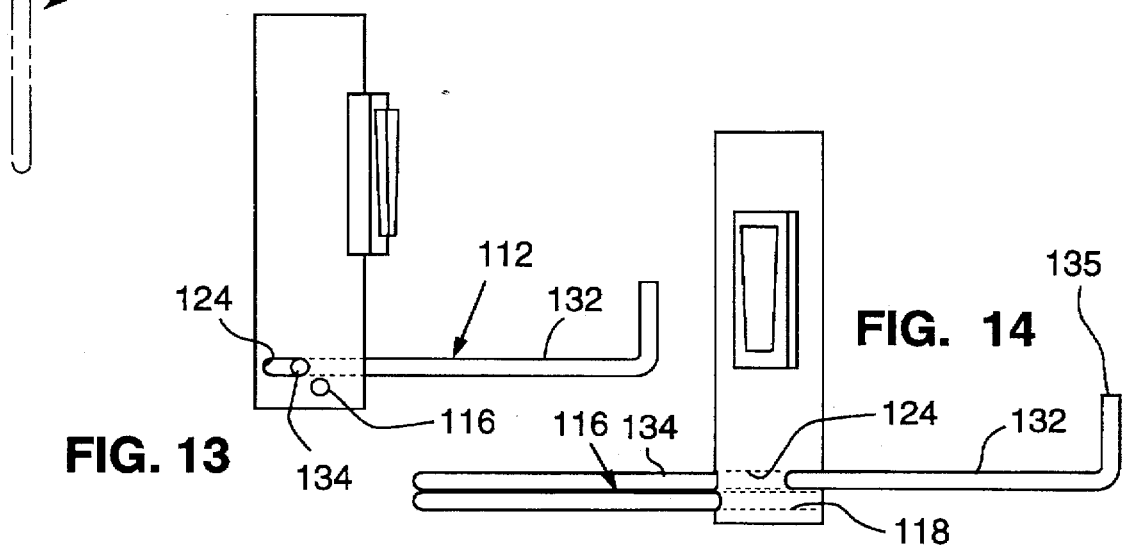
FIG. 13 is a front view of the second embodiment of FIG. 11.
Figure 14:
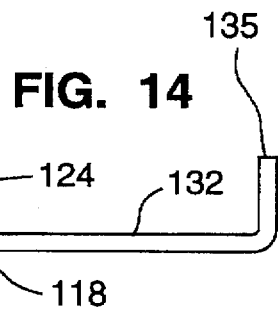
FIG. 14 is a side view of the second embodiment of FIG. 11.

During use, the angular rod 112 is withdrawn such that its distal portion 134 is close to and parallel with the straight rod as in FIGS. 11–14. After insertion, the angular rod 112 is advanced distally as indicated by arrows in FIGS. 11 and 12 to broaden the gap between the two parallel rods. Phantom lines in FIGS. 12 and 13 illustrate the positioning of angular rod 112 after it has been fully extended.

FIGS. 15 through 22 show additional rod configurations which utilize one fixed rod and one sliding rod. In the third, and preferred, embodiment of FIG. 15, a sliding rod 212 and a fixed rod 220 each have a substantially straight intermediate portion 222, 224 and an angled distal portion 226, 228. Fixed rod 220 has a proximal portion 230 that is substantially perpendicular to intermediate portion 224 and that extends generally axially from cylindrical lifting body 210. Sliding rod 212 has a proximal portion 232 having a first connecting member 234 slidably disposed within a bore (not shown) in the cylindrical body 210. A second connecting member 236 connects the first connecting member 234 with the intermediate portion 222 of the sliding rod 212. The angled distal portion 226 and the intermediate straight portion 222 of the slidable rod 212 are parallel to their counterparts 228, 224, respectively, on the fixed rod 220. The intermediate straight portion 222 of the slidable rod 212 is longer than that of the fixed rod 220.

Figure 19:
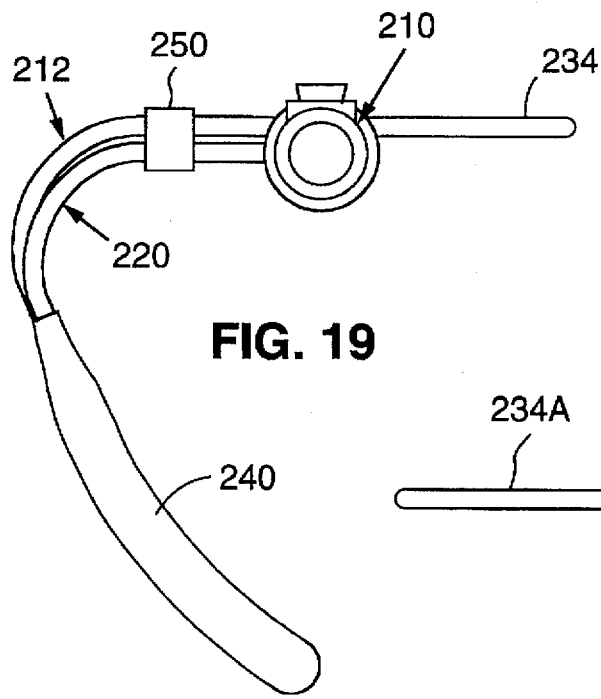
FIG. 19 is a top view of the preferred retraction system of FIG. 15 with the splines and keys not shown.
Figure 20:
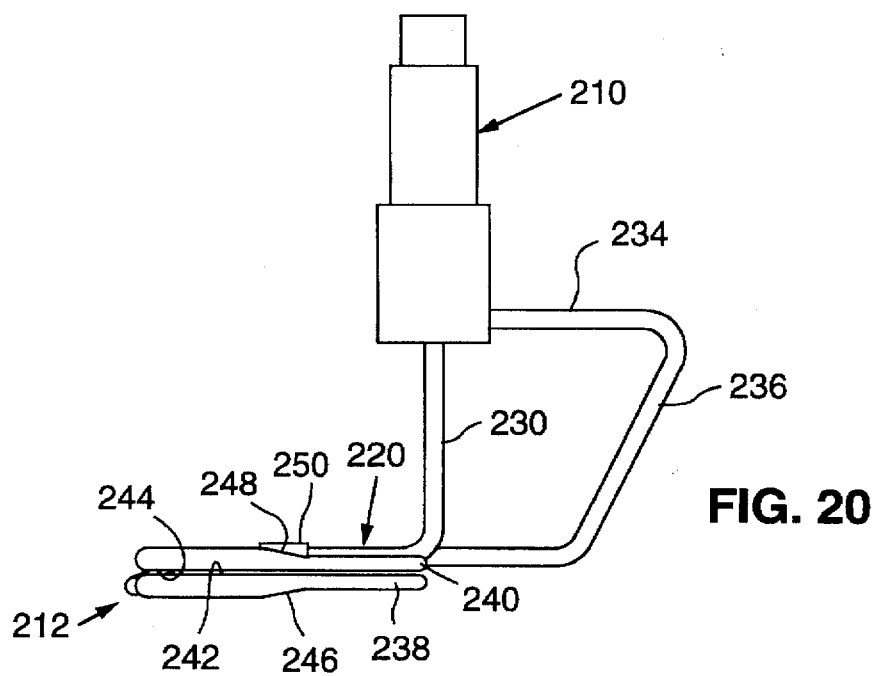
FIG. 20 is a side view of the preferred retraction system of FIG. 15 with the splines and keys not shown.

Each of the rods 212, 220 has a paddle 238, 240 fixed to its distal end. As shown in FIG. 20, each paddle has a substantially straight side 242, 244 and a tapered side 246, 248. The distal end 226 is curved slightly in the downward direction such that paddle 238 of the sliding rod 212 is located slightly below paddle 240 of the fixed rod 220. The paddles are oriented such that they are positioned with their substantially straight sides 242, 244 flat against each other when the slidable rod 212 is positioned in its most proximal position as shown in FIGS. 19 and 20. The paddles are shaped having an elongated cross-section near the distal end to reduce unit load on the patient's tissue and enhance insertion while positioned side by side. It should be noted that it is intended that similar paddles can be used in all embodiments of the invention described herein on load bearing rods, and configured to best suite the particular application intended.

A bearing 250 holds the intermediate straight portions 222, 224 such that they are adjacent and substantially parallel to one another. Sliding rod 212 is capable of sliding longitudinally within the bearing such that the intermediate straight portions 222, 224 and the angled portions 226, 228 remain substantially parallel to their respective counterpart as in FIG. 15.

The lifting body 210 of the preferred embodiment is configured to facilitate positioning of the rods prior to lifting by enabling rotation of the lifting rods 212, 220 relative to the lifting body. Because the configuration of the abdominal wall causes an irregular distribution of loading forces on the lifting rods during lifting, the lifting body is further configured to prevent the rods from rotating in response to torsional loading.

The lifting body 210 is comprised of a splined tubular section 216, a keyed column 252, and a base section 218. The splined tubular section 216 has a throughbore 254 having a splined proximal portion 256. A shoulder 258 is positioned in the throughbore 254 at the distal end of the tubular section 216. A dovetail mount 214 is connected to the exterior of the splined tubular section 216 for attachment to a mechanical lifting arm such as the one designated 80 in FIG. 10.

The keyed column 252 of the lifting body 210 is comprised of an elongate column having spaced keys 260 on its proximal section 261. The proximal section 261 forms a shoulder 266 with a middle section 268 which has a smaller diameter than the proximal section 261. Fixed to the distal end of the keyed column 252 is a rectangular block 270 which is in turn fixed to the proximal section 230 of fixed rod 220. The keyed column 252 of the lifting body 210 is proportioned to fit inside the throughbore 254 of the splined tubular section 216 with a compression spring 262 disposed around middle section 266 and supported by shoulder 258 as shown in FIGS. 17 and 18.

The keyed column 252 and the splined tubular section 216 are in turn disposed within a throughbore 264 in base section 218 of the lifting body 210. As shown in FIGS. 17 and 18, when the lifting body 210 is fully assembled, the keyed column 252 and the base section 218 are secured to one another by virtue of the rectangular block 270 of the keyed column 252 which is positioned below a rectangular opening 272 in the base section 218 and secured against a plate 274 surrounding the opening 272.

Figure 17:
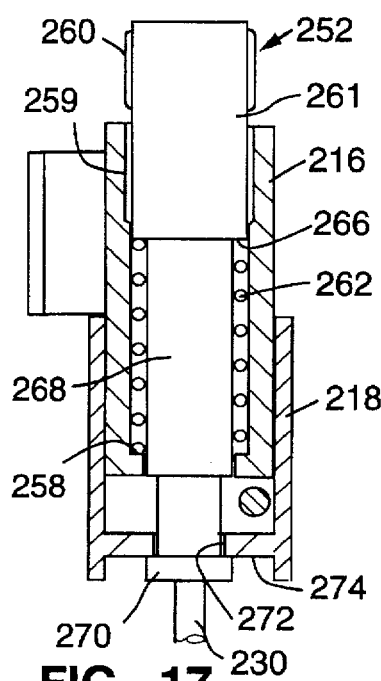
FIG. 17 is a cross-sectional side view of a portion of the lifting body of the preferred embodiment of FIG. 15 showing the positioning of its components prior to application of a lifting force.
Figure 18:
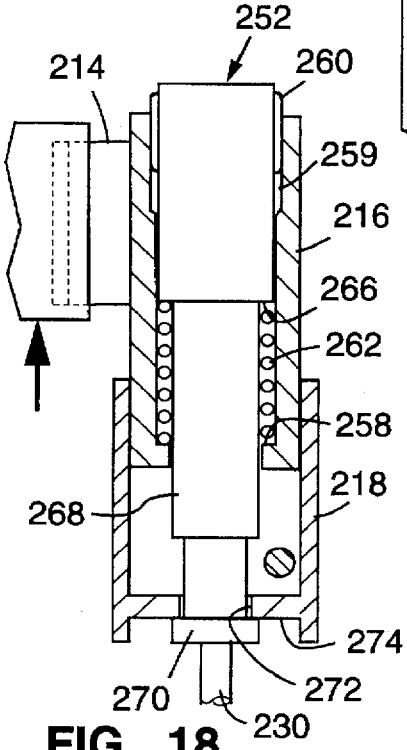
FIG. 18 is a cross-sectional side view of a portion of the lifting body of the preferred embodiment of FIG. 15 showing the positioning of its components during loading.

When the apparatus is in an unloaded state, the keys 260 of the keyed column 252 are positioned proximal of the splined tubular section 216, as shown in FIG. 17. When in this state, the keyed column 252 and the base section 218 are capable of rotating jointly about their common longitudinal axis while the splined tubular section 216 remains fixed. When tensile force is applied between the splined tubular section 216 and the base section 218, the base section 218 pulls the keyed column 252 such that it moves longitudinally in the distal direction within the throughbore 254 of the splined tubular section 216, causing keys 260 to become engaged with splines 259 on the splined tubular section 216. Engagement of the splines 259 and the keys 260 prevents rotation of the keyed column 252 and base section 218.

The spring serves to allow engagement of the keys 260 and splines 259 only when the tensile force exceeds a minimum level. Application of the tensile force between the splined tubular section 216 and the base section 218 causes spring 262 to be compressed between shoulders 258 and 266. The spring is preferably one having a spring constant that will prevent engagement of the keys 260 and splines 259 until the tensile load reaches approximately five pounds.

To use the preferred embodiment, the sliding rod 212 is positioned in its most proximal position such that the substantially straight sides 242, 244 of paddles 238, 240 are opposing each other as shown in FIG. 20. The paddles 238, 240 are next inserted into the abdominal cavity.

Figure 15:
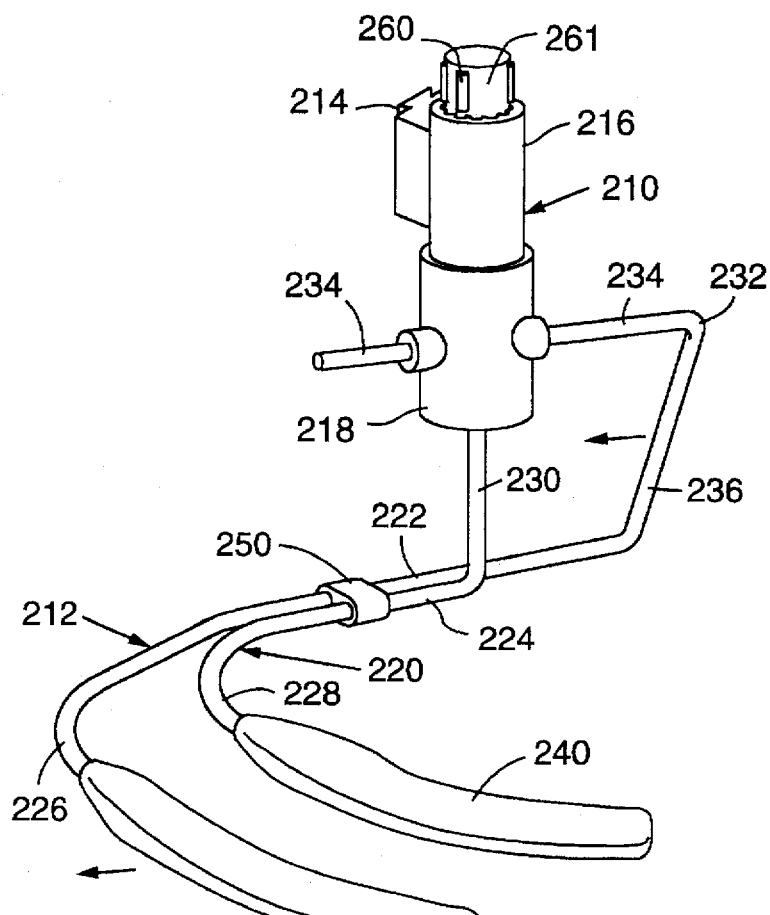
FIG. 15 is a perspective view of the third and preferred embodiment of a retraction system according to the invention.
Figure 16:
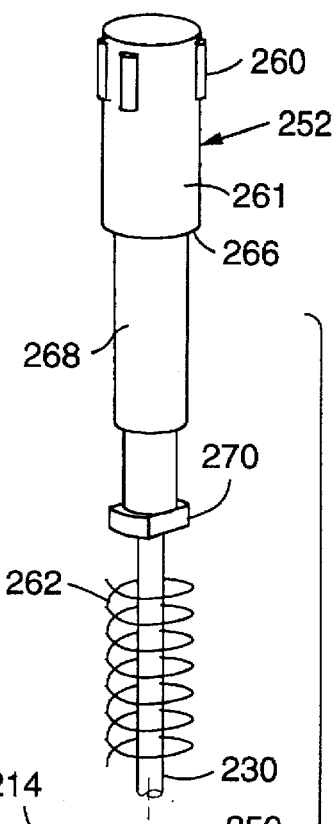
FIG. 16 is an exploded cross-sectional view of a portion of the lifting body of the preferred retraction system of FIG. 15.

Pushing second connecting member 236 towards the proximal portion 230 of the fixed rod 220 as indicated in FIG. 15 advances the angled portion 226 of the sliding rod 212 into the abdominal cavity beyond the angled portion 228 of the fixed rod 220. Because the bearing 250 holds the straight portions 222, 224 adjacent to each other, the parallel placement of the angled portions 226, 228 is maintained while the distance between them increases. Once the desired separation between the angled portions is reached, the dovetail connector 214 of the lifting body is connected to a lifting arm such as the one designated 80 in FIG. 10. The positioning of the rods within the abdominal cavity is next adjusted by rotating the base section 218 of the lifting body 210 relative to the splined tubular section 216. A lifting force is next applied to the lifting body 210 by the lifting arm. When the lifting force reaches five pounds, spring 262 will compress sufficiently to cause the keys 260 to engage with the splines 259 and to thereby prevent the rods from rotating out of the desired position during lifting.

Figure 21:
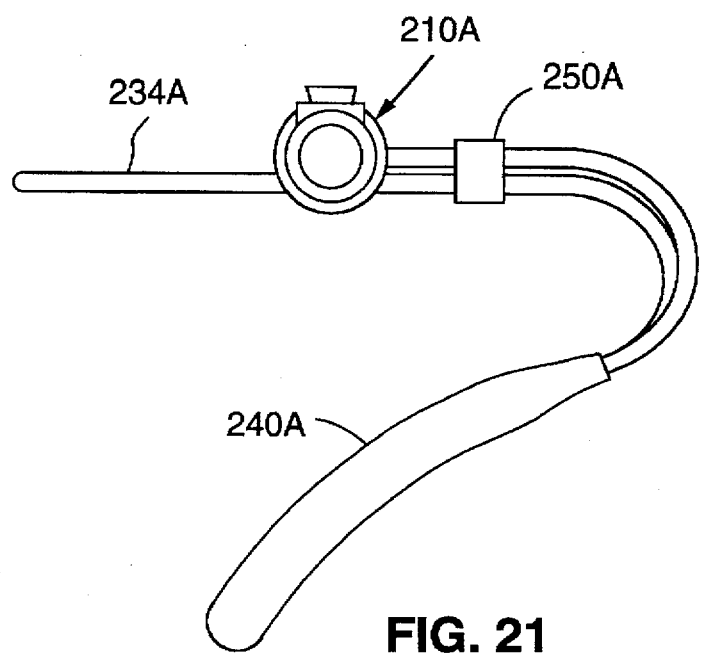
FIG. 21 is a top view of the preferred retraction system of FIG. 15 utilizing paddles configured for upper abdominal retraction.

The shapes and angles of the angled portions 238, 240 may be configured as required to provide optimal visualization of a particular region of the abdominal cavity. For example, the paddle 240A shown in FIG. 21 is preferable for use in the upper abdominal region, such as the epigastric region, because its concave curvature mimics the curvature of the rib cage. On the other hand, the paddle 240 shown in FIG. 19 is preferable for use in the larger lower abdominal region because the paddle shape defines a broad lifting area.

Figure 22:
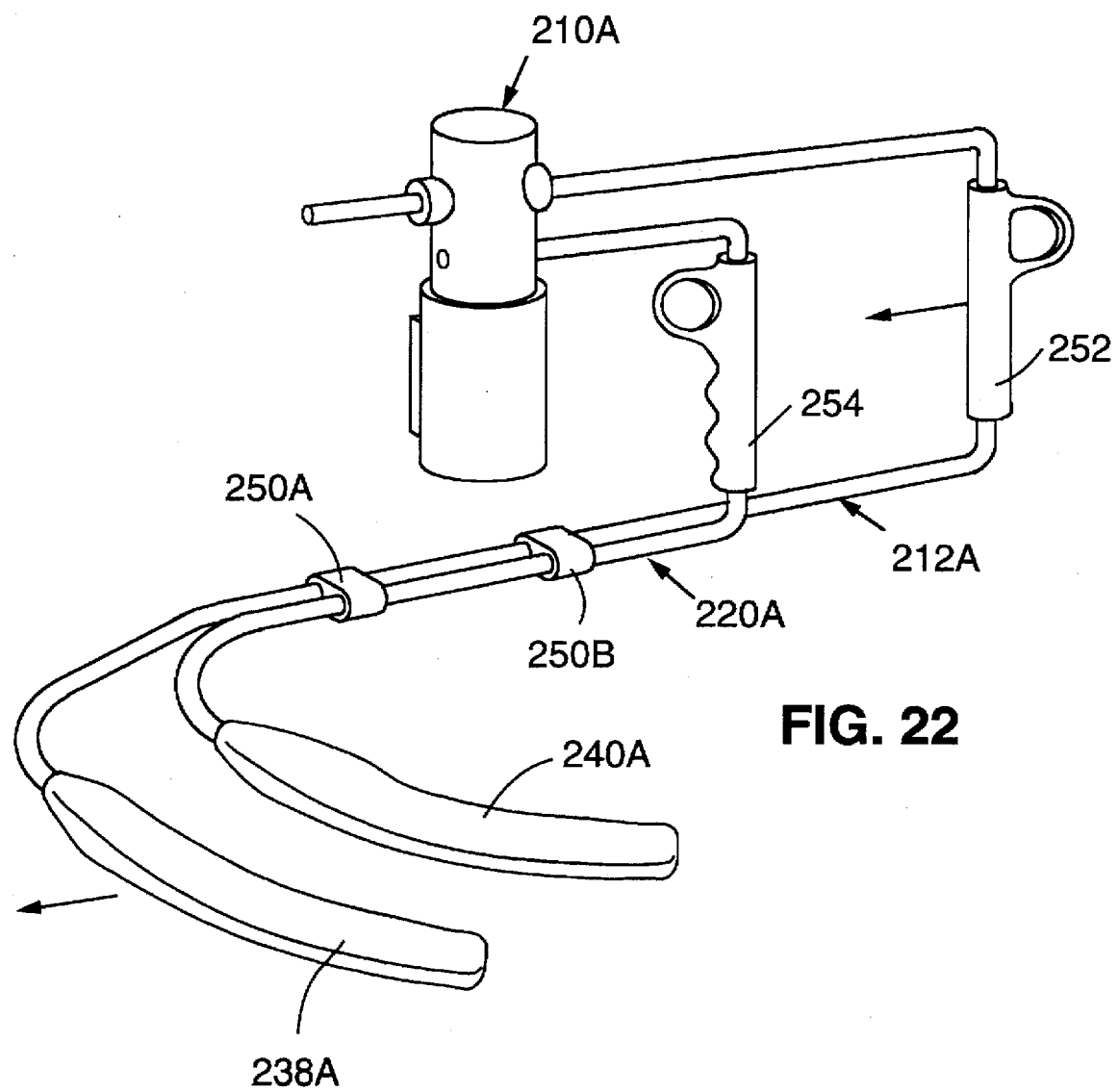
FIG. 22 is a perspective view of a fourth embodiment according to the present invention.

A fourth embodiment, which is a slight modification of the preferred embodiment is shown in FIG. 22. The fourth embodiment utilizes a sliding rod 212A and a fixed rod 220A, each connected to a lifting body 210A and held adjacent to each other by a pair of bearings 250A, 250B. The rods 212A, 220A are provided with handles 252, 254 which assist the user in pushing sliding rod 212A and thereby extending paddle 238A into the abdominal cavity in preparation for lifting.

Another alternative rod configuration is utilized in the fifth embodiment, designated 310 and shown in FIGS. 23–26. In this configuration, each rod 312 is comprised of proximal 314 and distal 316 straight portions joined at an approximate right angle. A handle 324 is provided at the proximal end of each rod. Two bores 318, 320 pass through the cylindrical body, designated 321, each entering on opposite sides of the cylindrical body 321 and exiting on the bottom face 322 of the cylindrical body as shown in FIG. 25. The rods are positioned with the proximal portions 314 disposed within the bores 318, 320 such that the distal portions 316 are positioned parallel to the bottom face 322 of the cylindrical body 321 and in side-by-side parallel relation with respect to each other as shown in FIG. 25.

During use, the handles 324 are used to advance the proximal portions 314 of the rods towards the cylindrical body, as indicated by arrows in FIG. 23, causing the distal portions 316 to advance from the bottom face 322 of the cylindrical body 321 as shown in FIG. 26, and to move laterally away from one another while maintaining their parallel relationship as shown in FIG. 24.

In another rod configuration, shown in the sixth embodiment in FIGS. 27 through 30, the cylindrical body is designated 410 and each rod 412 is comprised of a straight distal portion 414 joined at an approximate right angle to an arcuate proximal portion 416. Two bores 418, each having an arcuate path as shown in FIG. 29, pass from opposite sides of the cylindrical body 410 to the bottom face 420 of the cylindrical body. When the rods are in their proximal position, shown in FIG. 25, the straight distal portions of the rods are oriented in parallel to the bottom face 420 of the cylindrical body 410 and in side-by-side parallel relation with respect to each other. Advancing the proximal portions 416 of the rods in the direction indicated by arrows in FIG. 27 causes the distal portions 414 to advance further from the bottom face 420 of the cylindrical body along an arcuate path to their fully extended position, which is shown in phantom lines in FIG. 27. As shown in FIG. 28, the distal portions 414 remain substantially parallel to each other at all times when the rods are not loaded, although deflection of the rods may occur during lifting of the abdominal wall. Because the distal portions spread from each other along arched paths, this embodiment spaces the rods more widely than rods which are spread angularly and thus allows a larger area of the abdominal wall to be lifted.

The sixth embodiment may be configured to ensure simultaneous deployment of the rods. Referring to FIG. 30, a pair of rollers 422, 424 may be positioned inside the cylindrical body 410. Each roller is rotatable about a pin 426, 428 passing through its axis. A portion of the perimeter of each roller is in contact with that of the other roller, and a separate portion of the perimeter of each roller is in contact with the arcuate portion 416 of one of the rods. The pin 428 passing through the axis of roller 424 is connected to a knob 430 positioned on the exterior of the cylindrical body. Turning the knob 430 about its axis rotates the pin and thereby rotates roller 424. Rotation of roller 424 causes roller 426 to rotate due to the contacting portions of their perimeters. Rotation of the rollers 424, 426 causes movement of the rods due to the friction between the perimeters of the rollers and the rods 412.

In addition to embodiments such as those described above which deploy the rods by advancing them within bores in the cylindrical lifting body, other embodiments may be utilized which pivotally deploy the rods. One such embodiment, the seventh embodiment, is shown in FIGS. 31-33. This embodiment utilizes a cylindrical body 510 and J-shaped rods 512 each having a straight proximal portion 514 and an arcuate distal portion 516 joined at an elbow 518. The cylindrical lifting body 510 has two longitudinally oriented slots 520, each on an opposite side of the cylindrical lifting body from the other. Each slot 520 passes through the distal face 522 of the cylindrical lifting body, and a peg 524 crosses the distal end of each slot 520.

The rods 512 are positioned with their elbows 518 disposed within the distal portion of the slot 520 such that the rods 512 are pivotable around the pegs 524. When the rods are in their closed position, shown in FIG. 31, the straight proximal portions 514 of the rods 512 extend laterally from the cylindrical lifting body. The arcuate distal portions 516 of the rods extend through the distal ends of the slots 520 from the bottom face 522 of the cylindrical body 510 and are in side-by-side parallel relationship with each other, allowing the distal portions 516 of the rods 512 to be inserted into the abdominal cavity using a hooking motion. The rods 512 are deployed into the lifting position by moving the straight proximal portions 514 into the slots as indicated by arrows in FIGS. 31 and 33, thereby pivoting the rods around their elbows 518. The arcuate distal portions 516 are thereby pivoted laterally as indicated by arrows in FIGS. 31 and 33 to form the substantially circular lifting area 528 shown in FIG. 32. Rods 516 can alternatively be fabricated to be insertable into the abdominal cavity while perpendicular to lifting body 510, with one rod pivoting 180° to create the circular lifting area 528.

In a variation of this embodiment, an inflatable envelope (preferably an elastic or inelastic balloon) is secured to lifting body 510 near distal face 522 to retract surrounding tissue and provide an unobstructed path for deployment of pivoting rods 516. Such an envelope further serves as a supporting membrane across rods 516 when in the deflated state as rods 516 are deployed laterally, thereby preventing tissue from sagging between the rods.

In an eighth embodiment, the lifting body is cubical and has a variety of bores which allow the surgeon to fashion a rod configuration which will provide the most satisfactory visualization of the organs to be treated. As shown in FIG. 34, this alternative embodiment is comprised generally of a lifting body 610 mounted to the distal portion of a handle 614, retraction rods 612 for insertion into bores 616,618 in the lifting body 610, and a lifting grip 620 positioned at the proximal portion of the handle 614.

Referring to FIG. 35, the lifting body 610 is preferably cubic, although lifting bodies of various shapes are possible. Its size and shape are limited by a number of factors. During use, the lifting body will normally be placed in the abdominal cavity AA, FIG. 34, through a puncture opening or small incision BB and therefore should preferably be approximately 10-20 mm in length. Moreover, as will be described below, the lifting body 610 will be used to lift a portion of the abdominal wall CC. The upper face 622 of the lifting body 610 should thus have adequate surface area and geometry to accomplish this lifting without tearing or traumatizing the surrounding tissue.

Referring to FIGS. 36 through 38, several bores 616, 618 pass through the body from its rear face 624 to its forward face 626, lower face 628, and side faces 630. The bores 616 which will be used for lifting the abdominal wall are approximately parallel with the plane of the upper face 622 of the lifting body (i.e. parallel to the horizontal plane) so as to allow for even loading of the retraction rods inserted through the bores 616. These bores are intended to receive rods which will exert lifting forces on the abdominal wall. It is preferable to have these bores passing through the side faces 630 of the lifting body as shown in FIG. 37 so that retraction rods inserted into them will fan outward from the lifting body thereby maximizing the area of the abdominal wall subjected to the lifting forces of the rods. A selection of bores having various orientations may be provided to enable to surgeon to choose the configuration of rods that is most suitable for the size of the patient and the necessary amount of work space.

Several other bores 618 angle downward and pass through the lower portion of the forward face 626 of the lifting body. These are intended to receive rods which will be used for retracting abdominal organs or other tissue within or surrounding the abdominal cavity (collectively referred to herein as "abdominal organs") out of the way of the work space as described below. Bores which pass through the lower face 628 of the lifting body may also be provided. Various surgical procedures will require downward angles of varying degrees. For example, retraction of the liver requires a downward angle of approximately 45° from a horizontal plane while retraction of the bowel requires a downward angle of approximately 60°–70° from the horizontal plane.

Mounted to the handle 614 is a dovetail connector 632 which is provided for connecting the fan retractor to a lifting bar or holding bar 80. (See FIG. 34.)

The proximal portion of the handle 614 is formed into a lifting grip 620. The grip 620 provides a means for manipulating and temporarily lifting the lifting body and the portion of the abdominal wall surrounding it while the retraction rods are being inserted into the lifting body.

Various types of rods may be configured for use with the present retraction system. As shown, each rod 612 has an insertion end 644 for insertion through the bores 616,618 and into the abdominal cavity AA, and a stabilizing end 646 which extends laterally from the rod. The stabilizing end 646 is incapable of entering the bores and thereby prevents the rod 612 from falling into the abdominal cavity.

Retraction rods of differing lengths may be configured to provide retraction of abdominal organs located at varying distances from the lifting body. Rods for retracting the abdominal wall may be approximately 4–6" in length, while rods of approximately 10" in length may be needed for retracting the bowel, liver, and other organs. Long rods (not shown) may be constructed with adjustable stabilizing devices which allow the surgeon to choose the depth to which a longer retraction rod may be inserted and to lock the retraction rod in position against the rear face 624 of the body once it has reached the desired depth.

The rods may be constructed to taper slightly from the insertion end to the stabilizing end to facilitate movement of the rods as they pass into the abdominal cavity. The stiffness of the rods in the lifting direction, i.e., in the direction of the lifting handle, may be made to decrease distally from the stabilizing end. Distally reducing the stiffness of the rods enables them to bend to conform to the shape of the raised abdomen while having sufficient strength to provide the lifting force necessary. This spreads the lifting force evenly along the length of the rods instead of concentrating the lifting force towards their distal ends.

Figure 41:
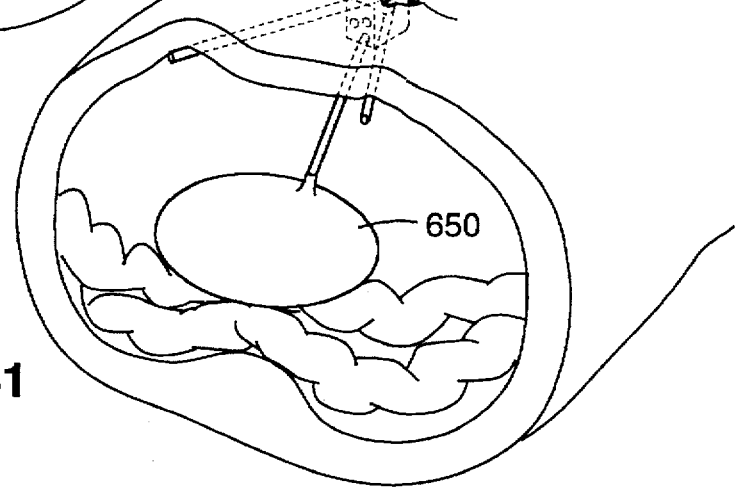
FIG. 41 is a perspective view, schematically showing the use of retraction rods for lifting retraction and a balloon retractor for abdominal organ retraction with the eighth embodiment.

Rods which may be expanded once they are inserted into the abdominal cavity may also be configured. Such a construction may be used to lock the rods within the bores at select positions relative to the body. As illustrated in FIG. 41, a balloon tipped retractor 612A having a hollow cannula 648 with an inflatable balloon 650 attached at its distal end and a valve 652 at its proximal end may be used for organ retraction.

The method for using the retractor according to the eighth embodiment will next be described.

Figure 39:
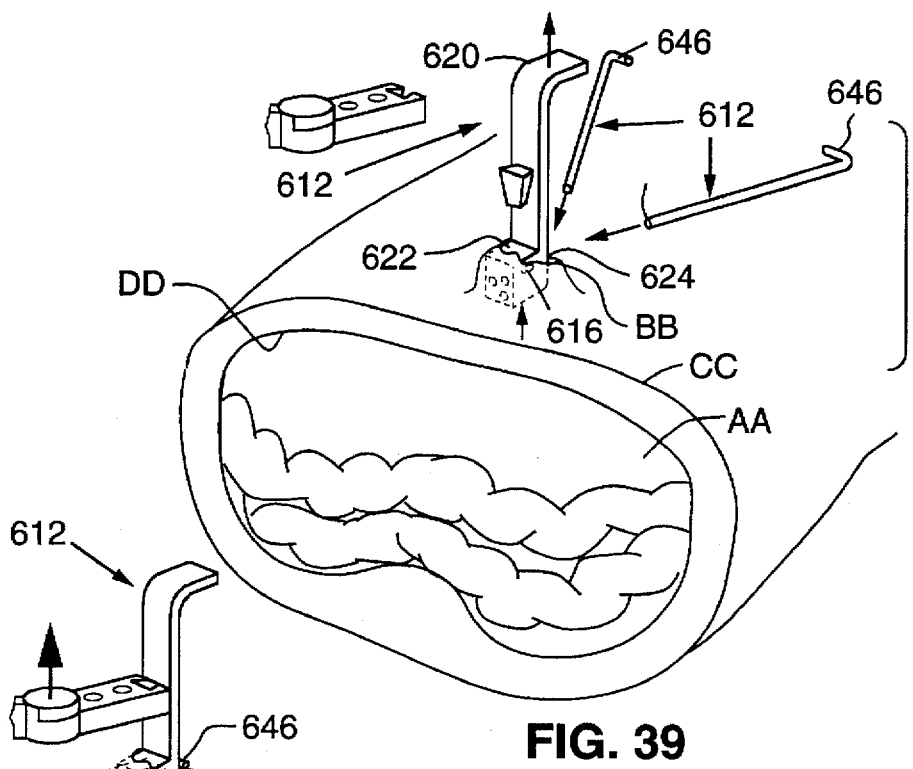
FIG. 39 is a perspective view, schematically showing the lifting body according to the eighth embodiment positioned in the puncture opening with the retraction rods in position for insertion through the lifting body.

An incision or trocar puncture BB is made in a suitable location in the abdominal wall. The lifting body 610 is inserted into the incision and positioned under the abdominal wall adjacent to the incision as shown in FIG. 39. The handle 614 is held such that it protrudes from the incision in a direction normal to the abdominal wall.

As indicated by arrows in FIG. 39, a lifting force is applied manually to the lifting grip 620 so that the lifting body 610 pulls the abdominal wall slightly upward in the direction of the lifting force. The entrances to the bores, which are at the rear face 624 of the lifting body are thus lifted above the incision. Retraction rods 612 are individually advanced through selected bores by inserting the insertion ends 644 of the retraction rods into the bores 616 from the rear face 624 of the lifting body and advancing them into the abdominal cavity AA such that they are in contact with the interior surface of the abdominal wall DD. The retraction rods 612 should be advanced until their stabilizing ends 646 abut the rear face 624 of the handle 614, preventing them from advancing further.

Figure 40:
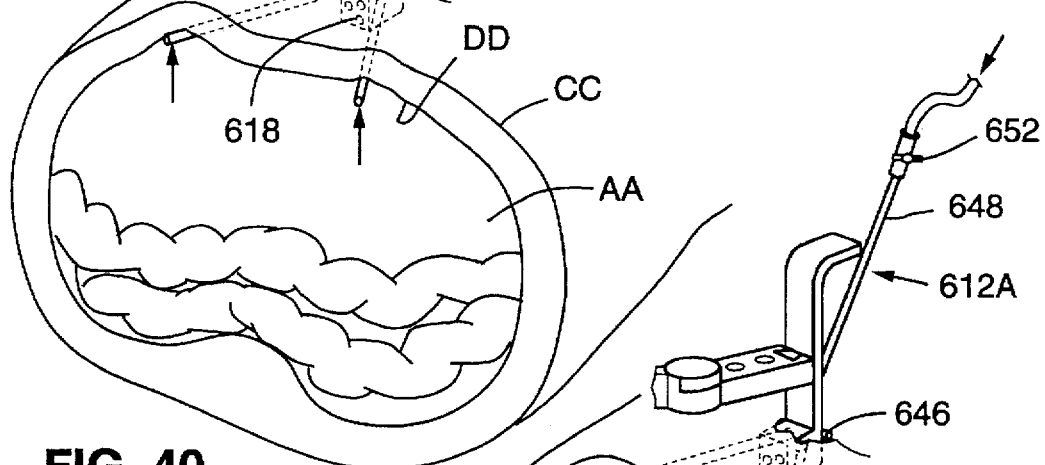
FIG. 40 is a perspective view, schematically showing the application of a lifting force to the eighth embodiment of the retraction system according the invention.

The handle is next connected at the dovetail connector 632 to a mechanical lifting device. The mechanical lifting device applies additional lifting force to the handle 614 as shown by arrows in FIG. 40, thereby raising the abdominal wall by causing the retraction rods 612 to push the abdominal wall from inside the abdominal cavity. Referring to FIG. 41, once the abdominal wall is raised, additional retraction rods such as the balloon retractor 612A may be inserted at downwardly-directed bore holes 618 so as to retract abdominal organs away from the surgeon's work space. If a balloon retractor 612A is used, the valve 652 is connected to a source of inflation gas, such as air or carbon dioxide, and gas is allowed to flow into the balloon 650 through the cannula 648 until the balloon is inflated as desired.

A ninth alternative embodiment is shown in FIGS. 42 through 49. This embodiment is comprised of a pair of lifting bodies 710 positioned in side-by-side relationship on a pair of dovetail mounts 715 connected to a dovetail wrist 714 for connecting the bodies to a lifting arm 80 (see FIG. 10), and a pair of lifting rods 712 suspended from the lifting bodies 710.

Figure 43:
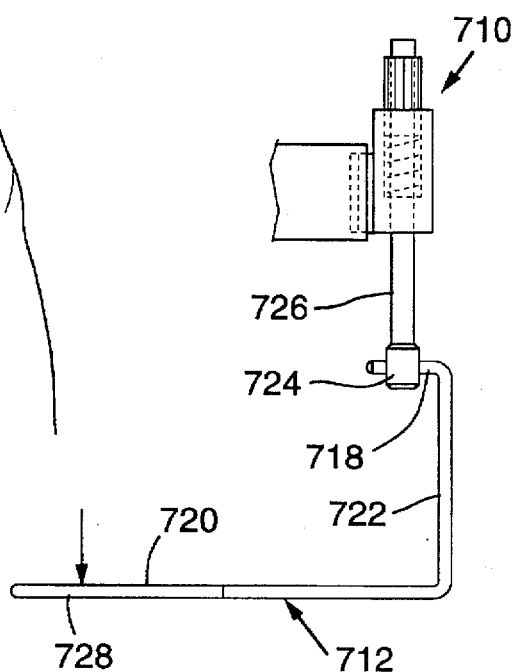
FIG. 43 is a side view of the ninth embodiment of FIG. 42.

Referring to FIG. 43, each retraction rod 712 is comprised of a connecting member 718, a retracting portion 720, and a substantially vertical support portion 722 connecting the two. The connecting member 718 is secured within a bore at a base 724 of a support column 726. The retracting portion 720 is substantially parallel to the connecting member 718.

Figure 42:
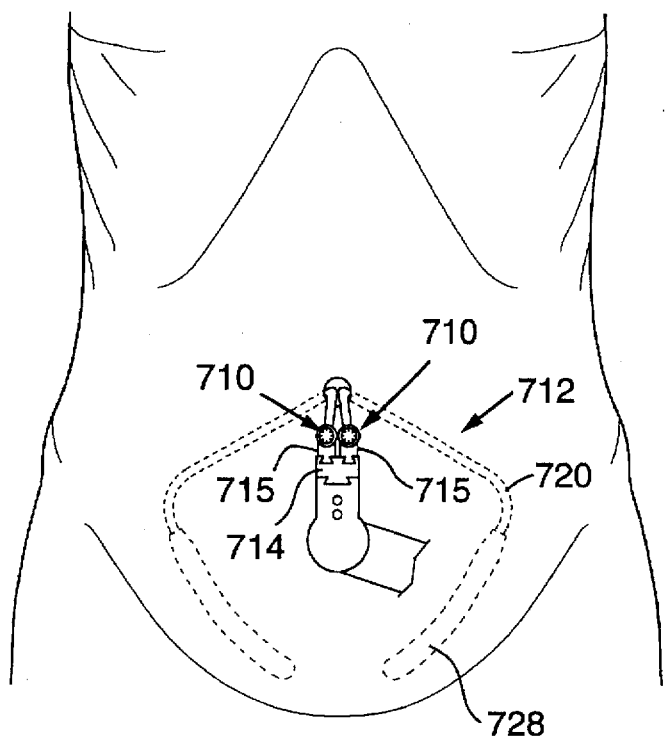
FIG. 42 is a top view of an ninth embodiment of a retraction system according to the invention schematically showing the device connected to a lifting arm and positioned within a lower abdominal region.

As shown in FIG. 42, the distal end of each retracting portion 720 is formed into a paddle 728. The retracting portions 720 are shaped such that when the apparatus is fully assembled for lifting, the region defined by the retracting portions 720 is approximately diamond-shaped as shown in FIG. 42. This shape, as well as the other shapes previously disclosed, is intended to profile the natural shape of the particular body cavity and surrounding anatomic features.

Figure 45:
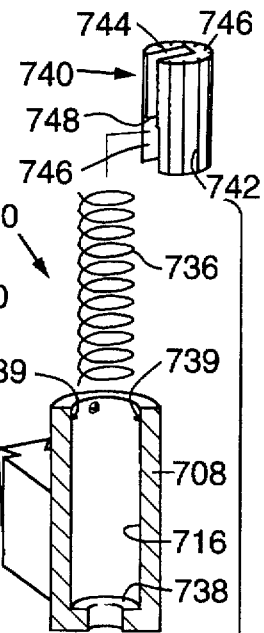
FIG. 45 is an exploded view of a lifting body of the ninth embodiment of FIG. 42.
Figure 47:
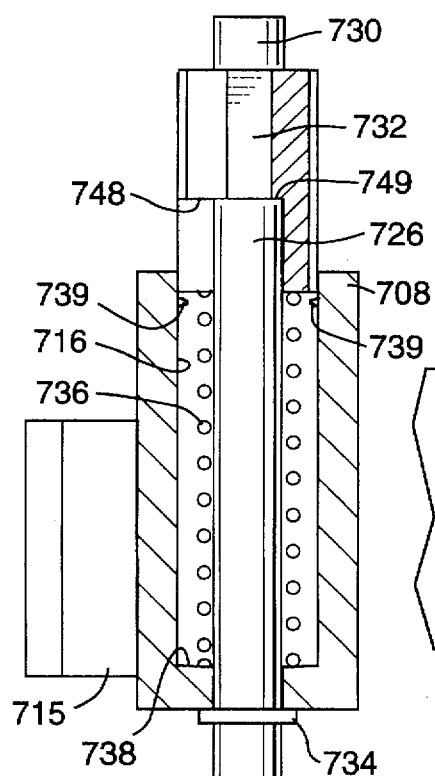
FIG. 47 is a side section view of a lifting body of the ninth embodiment of FIG. 42 showing the lifting body prior to loading.
Figure 48:
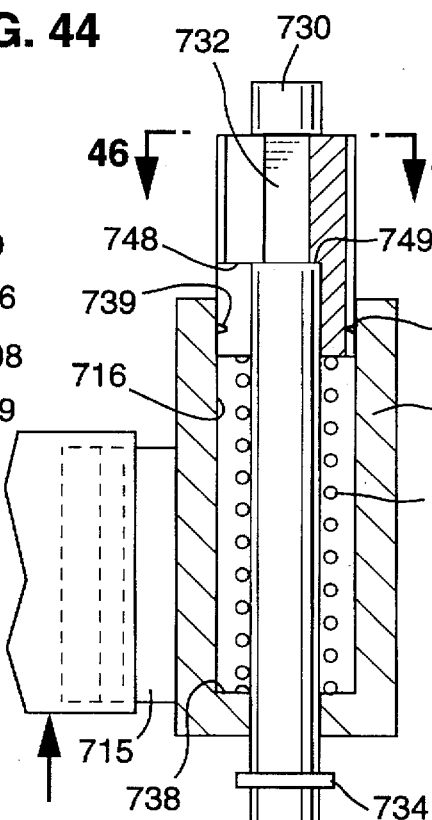
FIG. 48 is a side section view of a lifting body of the ninth embodiment of FIG. 42 showing the lifting body during loading.

Referring to FIG. 45, each lifting body 710 is comprised of a cylindrical body 708 having a throughbore 716 and a compression spring 736 positioned in engagement with a shoulder 738 in the throughbore 716. Spaced keys 739 are secured to the cylindrical body 708 within the throughbore 716 and extend into the throughbore as shown in FIG. 47.

Each support column 726 is comprised of an elongate member of circular cross-section proportioned for insertion through the throughbore 716 in the lifting body such that the spring 736 is disposed around it. Near a proximal head 730 of the support column 726 is a reduced-diameter portion 732 having a square cross-sect/on. Because the reduced-diameter portion 732 is cut out of the relatively wider support column 726, a ridge 749 is formed at the base of the reduced-diameter portion 732. The support column also has a locking ring 734 slidably disposed around it at a position distal of the reduced diameter portion 732.

Figure 46:
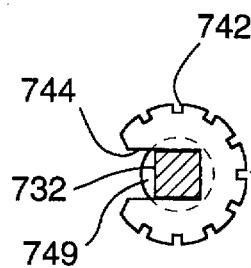
FIG. 46 is a top section view of a lifting body of the ninth embodiment of FIG. 42 taken along the plane designated 46—46 in FIG. 48.

The lifting body 710 further comprises a splined column cap 740 having spaced splines 742 extending longitudinally on the column cap 740. The column cap 740 is cylindrical and has squared 744 and rounded 746 cut-out portions which form a continuous passage longitudinally through it and which extend laterally to give the column cap a substantially C-shaped cross-section as shown in FIG. 46. The diameter of the rounded cut-out portion 746 is slightly greater than that of the squared cut-out portion 744 such that a shoulder 748 is formed between them. The squared cut-out portion 744 is proportioned to mate with the squared, reduced diameter portion 732 of the support column 726.

To assemble the apparatus for use, the support column 726 is inserted through the throughbore 716 of the cylindrical body 708 such that the spring 736 is disposed around it and such that the squared reduced diameter portion 732 protrudes proximally of the cylindrical body 708. The splined column cap 740 is positioned around the support column 726 with its squared cut-out portion 744 engaged with the squared portion 732 of the support column 726 beneath the head 730 such that shoulder 748 of the splined column cap 742 is supported by the ridge 749 on the support column 732. Joining the squared cross-sections of the support column 726 and the splined column cap 740 causes these components to be keyed together and thus incapable of rotating relative to each other.

Engaging the column cap 740 with the support column as described above causes the column cap 740 to be disposed partially within the throughbore 716 of the cylindrical body 708 near the proximal end of the lifting body 710 such that its distal end is supported by the spring 736 slightly above the level of the keys 739. When the apparatus is not loaded, the keys are positioned distal of the splined column cap, in the longitudinal direction. Thus, prior to loading, the keys and the splines are not engaged with each other and thus allow for the splined column cap 740 and support column 726 to be rotated as a single unit about their common longitudinal axis.

To use the ninth alternative embodiment, the lifting arm is positioned such that it hovers slightly above a puncture opening in an abdominal cavity as shown in FIG. 42. The dovetail mounts 715 are attached to dovetail wrist 714 which is then attached to a dovetail connector on the lifting arm 80 (see FIG. 10). Each paddle 728 is separately inserted into the puncture opening in the abdominal cavity and its respective support column 726 is subsequently inserted longitudinally into one of the cylindrical bodies 708 and held within the cylindrical body using the splined column cap 740 as described above.

The splined column cap and the support column are next rotated about their column longitudinal axis until the paddles 728 are in the desired position within the abdominal cavity. The lifting arm 80 is then raised to lift the abdominal wall.

The design of the lifting body 710 is such that the paddles may be rotated into the desired orientation prior to lifting and then secured against further rotation after a lifting force is applied. When, during lifting, a tensile force is applied to the apparatus in the direction indicated by arrows in FIG. 48, the support column 726 pulls down on the splined column cap 740. The loading on the splined column cap 740 causes it to move longitudinally within the cylindrical body 708 and to thereby compress the compression spring 736. When the downward loading reaches 5 lb, the splined column cap 740 advances far enough in the longitudinal direction for each of the keys positioned within the throughbore 716 in the lifting body to mate with a spline 742 on the exterior of the splined column cap 740. The lock caused by the mating of the keys and the splines prevents rotation of the splined column cap about its longitudinal axis and thus prevents rotation of the support column which is fixed to the splined column cap. Thus any torsional force caused by the pull of the abdominal wall on the paddles 728 during lifting will not rotate the paddles out of position.

If desired, the locking ring 734 (FIG. 45) may be advanced along the support column 726 towards the cylindrical body 708 until it is positioned just below the cylindrical body with the cylindrical body supported by it. Doing so locks the relative positioning of the support column 726 and the cylindrical body 708 so as to maintain engagement of the splines and the keys to prevent rotation of the paddles 728 even when no load is applied to the apparatus.

Figure 49:
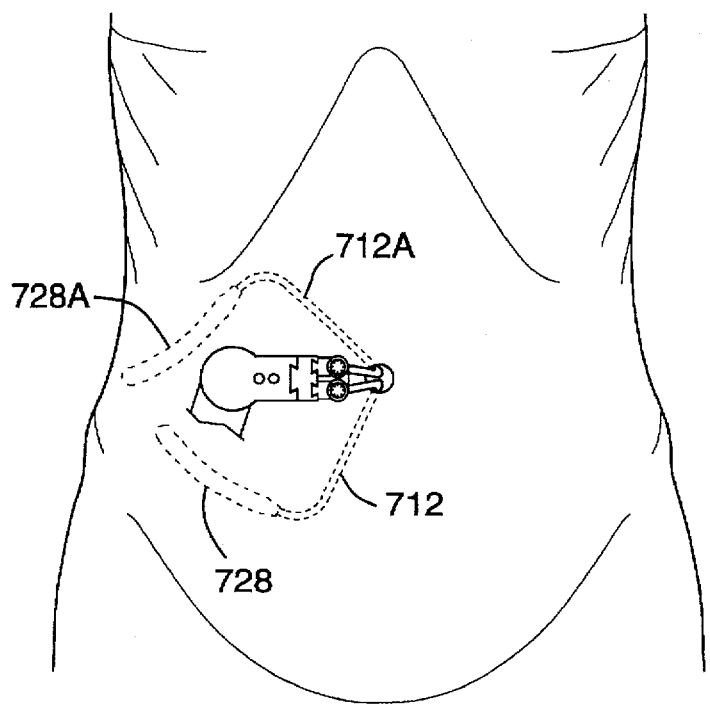
FIG. 49 is a top view of the ninth embodiment with a modified paddle and schematically showing the device laterally positioned within an abdominal region.
Figure 44:
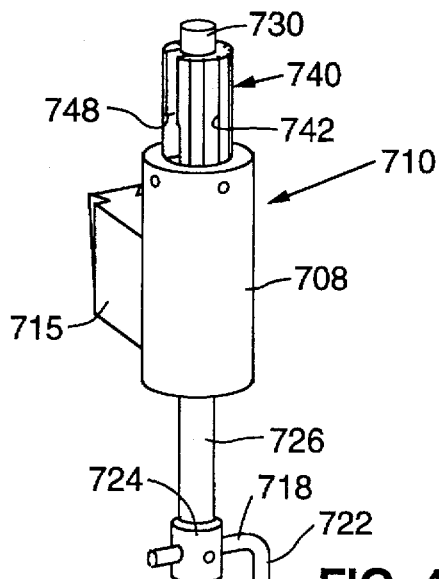
FIG. 44 is a perspective view of a lifting body of the ninth embodiment of FIG. 42.

In this and all other embodiments, the retraction rods may be configured in varying shapes so as to enable appropriate shapes to be chosen for particular procedures. For example, as shown in FIG. 49, in certain procedures, such as those requiring retraction of the lateral portion of the abdominal wall, rods 712, 712A having differing shapes may be used.

CONCLUSION

While the present invention has been described with respect to specific embodiments having varying features, it should be understood that the various features might be combined so as to create additional embodiments. For example, the paddle shapes and construction shown for one embodiment might be incorporated into another embodiment. The invention is not intended to be limited by the specifics of the embodiments which have been illustrated and described, but rather is defined by the accompanying claims.

We claim:

1. An apparatus for laparoscopically lifting a body wall, the apparatus comprising:

a lifting body capable of receiving a lifting force, the lifting body having a longitudinal axis;

a first lifting rod having a proximal section carried by the lifting body and further having a distal section;

a second lifting rod carried by the lifting body and having a proximal section and a distal section;

means mounting the first lifting rod for linear movement relative to the lifting body and independently of the second lifting rod between a condition where the distal sections of the first and second lifting rods are proximal to each other for insertion through a small laparoscopic incision of limited area in the body wall and a lifting position in which the distal section of the first lifting rod is spaced from the distal section of the second lifting rod for interior engagement by the distal sections of an area of the body wall exceeding the limited area of the small laparoscopic incision and in which the distal sections occupy a lifting plane which extends transversely across the longitudinal axis of the lifting body, the first lifting rod mounted for movement in a direction of movement which is transverse to the longitudinal axis of the lifting body;

wherein the lifting body is moveable to an elevated condition following insertion of the lifting rods through the incision, and wherein the apparatus further comprises means attachable to the lifting body for supporting the lifting body in the elevated condition with the lifting rods in the lifting position and for imparting a lifting force to the lifting body.

2. The apparatus of claim 1 wherein the distal section of the first lifting rod is fixed in angular relation to the proximal section and the first lifting rod is mounted to the lifting body such that linear movement of the proximal section produces rectilinear movement of the distal section.

3. The apparatus of claim 2 wherein the distal sections of the first and second lifting rods are substantially parallel when in the first and second positions.

4. The apparatus of claim 1 wherein:
the lifting body further comprises:
   a first body portion and a second body portion joined for relative rotational movement therebetween, the first and second lifting rods mounted to the second body portion; and
   locking means for preventing relative rotational movement of the first and second body portions when an excess of a predetermined loading force is delivered to the lifting rods.

5. The apparatus of claim 1 wherein the lifting body further comprises at least one bore passing through the lifting body, the bore proportioned for receiving the first or second lifting rod.

6. An apparatus for lifting a body wall, the apparatus comprising:
   a lifting body capable of receiving a lifting force, the lifting body having a longitudinal axis;
   a first lifting rod receivable by the lifting body for select extension laterally of the lifting body;
   a second lifting rod receivable by the lifting body, the first lifting rod capable of being extended independently of the second lifting rod;
   the first lifting rod linearly moveable relative to the lifting body and independently of the second lifting rod between a condition where a distal portion of the first lifting rod is proximal to a distal portion of the second lifting rod for insertion through a small laparoscopic incision of limited area in the body wall, and a lifting condition in which the distal portions of the first and second rods are spaced from one another for interior engagement of an area of the body wall exceeding the limited area of the small laparoscopic incision and in which the distal portions of the first and second rods occupy a lifting plane which extends transversely across the longitudinal axis of the lifting body;
   wherein the lifting body is moveable to an elevated condition following insertion of the lifting rods through the incision, and wherein the apparatus further comprises means attachable to the lifting body for supporting the lifting body in the elevated condition with the lifting rods in the lifting condition and for imparting a lifting force to the lifting body.

7. The apparatus of claim 6 wherein the means mounting the first and second lifting rods includes at least one bore in the lifting body proportioned for receiving the first lifting rod.

8. An apparatus for lifting the abdominal wall, the apparatus comprising:
   a lifting body capable of receiving a lifting force, the lifting body having a longitudinal axis and including a pair of bores;
   a first lifting rod at least partially disposed within one of the pair of bores for select extension laterally of the lifting body, the first lifting rod including a distal portion and a proximal portion joined together at an angle, the distal portion being extendable laterally of the lifting body; and
   a second lifting rod having proximal and distal portions, the second lifting rod at least partially disposed within one of the bores and fixed to the lifting body, the first lifting rod capable of being extended between a condition where a distal portion of the first lifting rod is adjacent to a distal portion of the second lifting rod for insertion through a small laparoscopic incision of limited area in the abdominal wall, and a lifting condition in which the distal portions of the first and second rods are spaced from one another for interior engagement of an area of the abdominal wall exceeding the limited area of the small laparoscopic incision and in which the distal portions of the first and second rods occupy a lifting plane which extends transversely across the longitudinal axis of the lifting body.

9. The apparatus of claim 8 wherein:
the distal portions of the first and second lifting rods are substantially arcuate, and
the distal portions of the first and second lifting rods are substantially parallel when the rods are in their first and second relative positions.

10. The apparatus of claim 9 wherein:
the lifting body further comprises:
   a first body portion and a second body portion joined for relative rotational movement therebetween, the first and second lifting rods mounted to the second body portion; and
   locking means for preventing relative rotational movement of the first and second body portions when in excess of a predetermined loading force is delivered to the lifting rods.

11. An apparatus for lifting a body wall, the apparatus comprising:
   a lifting body capable of receiving a lifting force, the lifting body having a longitudinal axis and further including a bore;
   a first lifting rod carried by the lifting body and slidable within the bore for select extension laterally of the lifting body, the first lifting rod including a distal portion and a proximal portion;
   a second lifting rod having proximal and distal portions, the second lifting rod fixed to the lifting body, the first lifting rod linearly extendable between a first condition where a distal portion of the first lifting rod is adjacent to a distal portion of the second lifting rod and a second condition in which the distal portions of the first and second rods are spaced from one another and in which the distal portions of the first and second rods occupy a lifting plane which extends transversely across the longitudinal axis of the lifting body;
   wherein the lifting body is moveable to an elevated condition following insertion of the lifting rods through the incision, and wherein the apparatus further comprises means attachable to the lifting body for supporting the lifting body in the elevated condition with the lifting rods in the lifting condition and for imparting a lifting force to the lifting body.

12. The apparatus of claim 11 wherein the distal portions of the first and second lifting rods are substantially parallel when the first lifting rod is in the first and second conditions.

13. The apparatus of claim 11 wherein:
the distal portions of the first and second lifting rods are substantially arcuate; and the distal portions of the first and second lifting rods are substantially parallel when the first lifting rod is in the first and second conditions.

14. An apparatus for lifting a body wall, the apparatus comprising:
- a lifting body capable of receiving a lifting force, the lifting body having a longitudinal axis and a pair of bores;
- a first lifting rod partially disposed within one of the pair of bores for select extension laterally of the lifting body; and
- a second lifting rod partially disposed within one of the pair of bores, the first lifting rod capable of being extended independently of the second lifting rod;
- the first and second lifting rods linearly moveable relative to the lifting body between a first relative condition where a distal portion of the first lifting rod is proximal to a distal portion of the second lifting rod for insertion through a small laparoscopic incision of limited area in the body wall, and a second relative condition in which the distal portions of the first and second rods are spaced from one another for interior engagement of an area of the body wall exceeding the limited area of the small laparoscopic incision and in which the distal portions of the first and second rods occupy a lifting plane which extends transversely across the longitudinal axis of the lifting body.

15. The apparatus of claim 14 wherein the distal portions of the first and second lifting rods are substantially parallel when in the first and second relative conditions.

16. The apparatus of claim 14 wherein the lifting body further comprises:
- a first body portion and a second body portion joined for relative rotational movement therebetween, the first and second lifting rods mounted to the second body portion; and
- locking means for preventing relative rotational movement of the first and second body portions when in excess of a predetermined loading force is delivered to the lifting rods.

17. An apparatus for lifting the abdominal wall, the apparatus comprising:
- a lifting body capable of receiving a lifting force, the lifting body having a longitudinal axis and including a bore;
- a first lifting rod at least partially disposed within the bore, the first lifting rod including a distal portion and a proximal portion extending laterally of the distal portion, the distal portion being linearly extendable laterally of the lifting body; and
- a second lifting rod carried by the lifting body and having proximal and distal portions, the first lifting rod extendable relative to the lifting body and independently of the second lifting rod between a condition where a distal portion of the first lifting rod is adjacent to a distal portion of the second lifting rod and a lifting condition in which the distal portions of the first and second rods are spaced from one another and in which the distal portions of the first and second rods occupy a lifting plane which extends transversely across the longitudinal axis of the lifting body.

18. The apparatus of claim 17 wherein the distal portions of the first and second lifting rods are substantially parallel when the first lifting rod is in the first and second conditions.

19. The apparatus of claim 17 wherein:
- the distal portions of the first and second lifting rods are substantially arcuate; and
- the distal portions of the first and second lifting rods are substantially parallel when the first lifting rod is in the first and second conditions.

* * * * *